(12) United States Patent
Tomlinson

(10) Patent No.: US 8,114,096 B2
(45) Date of Patent: Feb. 14, 2012

(54) ATRAUMATIC CIRCUMCISION APPARATUS AND METHOD OF USING SAME

(76) Inventor: David R. Tomlinson, Wakefield, RI (US)

( * ) Notice: Subject to any disclaimer, the term of this patent is extended or adjusted under 35 U.S.C. 154(b) by 141 days.

(21) Appl. No.: 12/653,275

(22) Filed: Dec. 10, 2009

(65) Prior Publication Data

US 2010/0168757 A1    Jul. 1, 2010

Related U.S. Application Data

(63) Continuation-in-part of application No. 11/768,808, filed on Jun. 26, 2007, now Pat. No. 7,806,902, and a continuation-in-part of application No. 11/571,120, filed as application No. PCT/US2005/022404 on Jun. 23, 2005, now Pat. No. 7,879,044.

(60) Provisional application No. 61/121,415, filed on Dec. 10, 2008, provisional application No. 60/816,798, filed on Jun. 26, 2006, provisional application No. 60/583,259, filed on Jun. 25, 2004.

(51) Int. Cl.
*A61B 17/32* (2006.01)
(52) U.S. Cl. ...................................................... 606/118
(58) Field of Classification Search ............... 227/175.1, 227/175.2, 176.1, 178.1, 179.1, 180.1, 181.1; 24/522, 528; 606/118, 120, 131, 157, 205, 606/207, 208
See application file for complete search history.

(56) References Cited

U.S. PATENT DOCUMENTS

| | | |
|---|---|---|
| D119,180 S | 2/1940 | Goldstein |
| 2,272,072 A | 2/1942 | Ross |
| 2,353,647 A | 7/1944 | Carmichael |
| 2,376,893 A * | 5/1945 | Baker ............................ 606/118 |
| 2,376,894 A * | 5/1945 | Baker ............................ 606/118 |
| 2,533,373 A | 12/1950 | Hinckley et al. |
| 2,620,800 A | 12/1952 | Powers |
| 2,646,046 A | 7/1953 | Maryan |
| 2,646,047 A | 7/1953 | Bronstein |
| 2,688,969 A | 9/1954 | Livoti |
| 1,765,319 A | 6/1960 | Williams |
| 3,050,065 A | 8/1962 | Grossman |
| 3,056,407 A | 10/1962 | Kariher et al. |
| 3,072,126 A | 1/1963 | Fenton |
| 3,166,075 A | 1/1965 | Kebel |
| 3,392,728 A * | 7/1968 | Bone et al. .................... 606/118 |
| 3,473,533 A | 10/1969 | Freda |
| 3,732,869 A | 5/1973 | Bronstein |
| 3,757,787 A | 9/1973 | Gottlieb |
| 3,789,848 A | 2/1974 | Honjyo |
| 3,802,439 A | 4/1974 | Baumgarten |
| 3,874,389 A | 4/1975 | Baumgarten |
| 5,163,943 A | 11/1992 | Mohiuddin et al. |

(Continued)

OTHER PUBLICATIONS

Australian Patent Office communication, mailing date May 8, 2008, Examiner's first report on Australian patent application No. 2005267242.

(Continued)

*Primary Examiner* — Ryan Severson
*Assistant Examiner* — Jonathan W Miles
(74) *Attorney, Agent, or Firm* — Peter J. Borghetti

(57) ABSTRACT

A disposable neonatal circumcision device that secures the foreskin of the penis in a precise location, applies radially circumferential clamping, and delivers a longitudinal circumferential cutting device along the path precisely controlled by the device itself, not the operator, ensuring the incision to the clamped foreskin is made in the precise location, independent of the operator.

7 Claims, 30 Drawing Sheets

U.S. PATENT DOCUMENTS

| | | | |
|---|---|---|---|
| 6,193,129 B1 * | 2/2001 | Bittner et al. | 227/180.1 |
| 6,623,494 B1 * | 9/2003 | Blatter | 606/153 |
| 6,660,012 B2 | 12/2003 | Lahiji | |
| 6,780,194 B2 | 8/2004 | Freedman et al. | |
| 6,959,851 B2 * | 11/2005 | Heinrich | 227/175.1 |
| 7,879,044 B2 * | 2/2011 | Tomlinson | 606/118 |
| 7,975,895 B2 * | 7/2011 | Milliman | 227/179.1 |
| 2001/0039399 A1 | 11/2001 | Bierman | |

OTHER PUBLICATIONS

Canadian Patent Office communications, mailing date May 9, 2008, Examiner's first report on Canadian patent application No. 2,571,934.

Canadian Patent Office communications, dated May 13, 2009, Examiner's second report on Canadian patent application No. 2,571,934.

Patent Cooperation Treaty Notification of Transmittal of the International Search Report and the Written Opinion of the International Searching Authority, or the Declaration, mailing date Jan. 25, 2006, PCT international application No. PCT/US05/22404.

Patent Cooperation Treaty Written Opinion of the International Searching Authority, mailing date Jan. 25, 2006, PCT international application No. PCT/US05/22404.

United States Patent and Trademark Office communication, mailing date Jun. 26, 2009, Examiner's first report on U.S. Appl. No. 11/768,808.

United States Patent and Trademark Office communication, mailing date Jul. 10, 2009, Examiner's first report on U.S. Appl. No. 11/768,817.

* cited by examiner

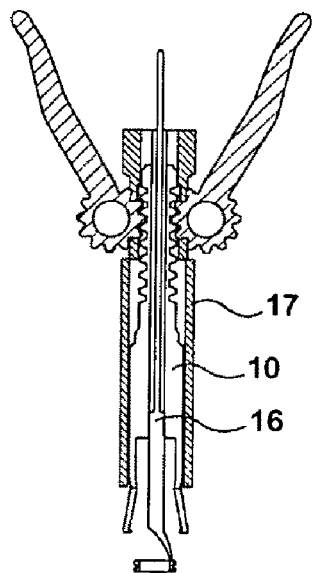
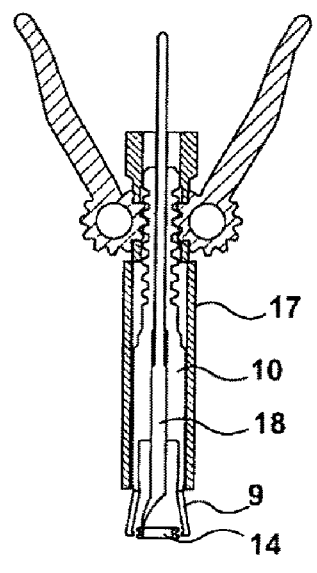
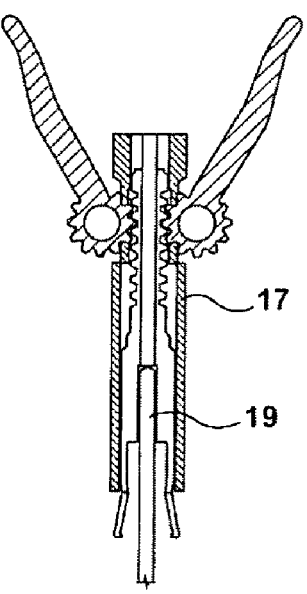
FIG. 10  FIG. 11  FIG. 12
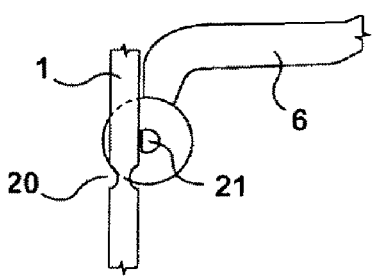
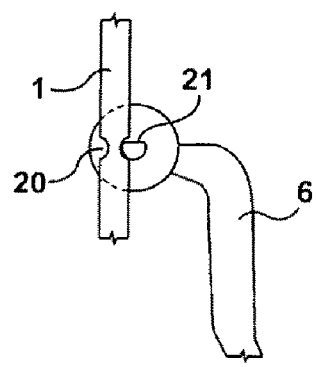
FIG. 13  FIG. 14

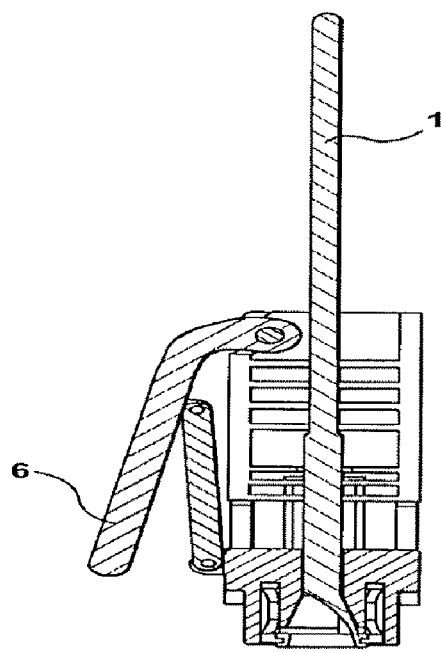
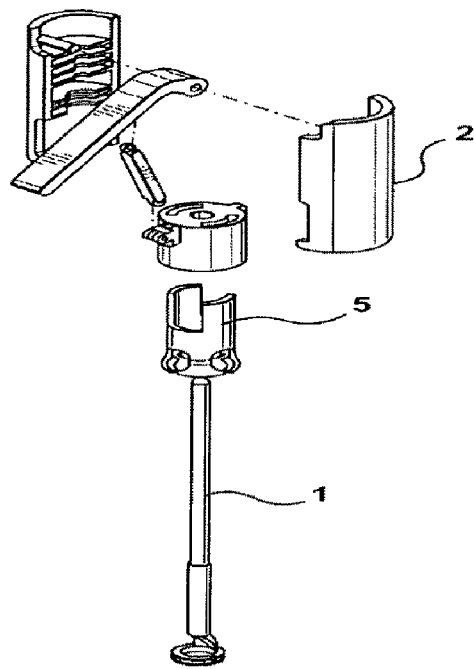
FIG. 19
FIG. 20

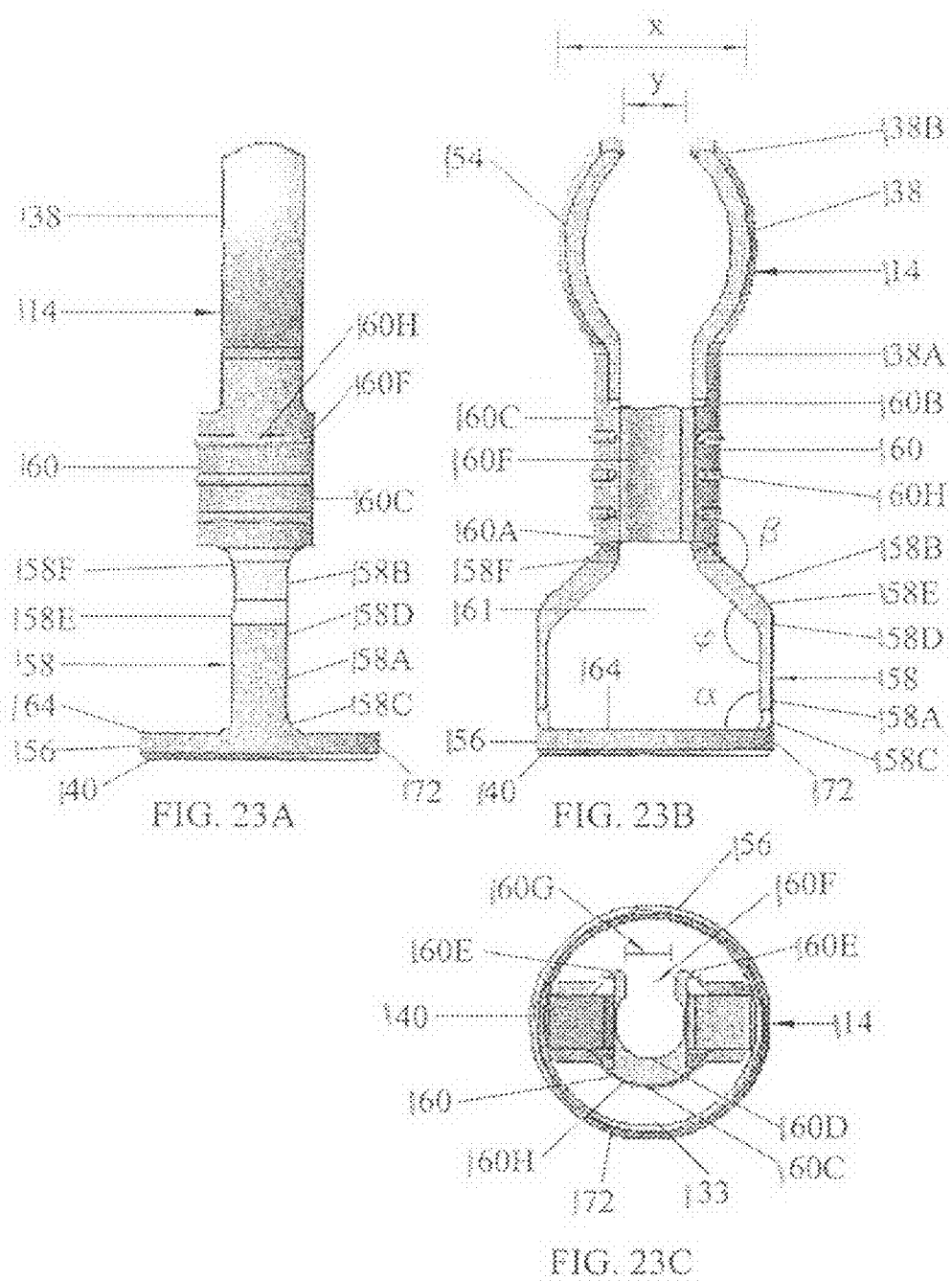

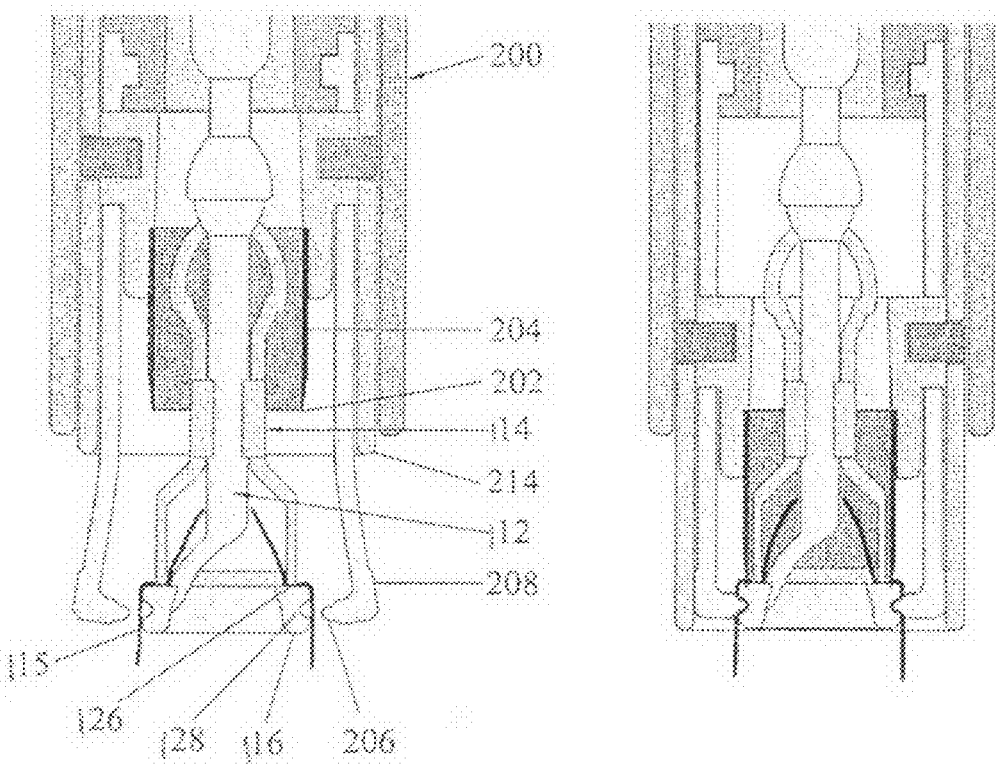
FIG. 31A
FIG. 31B
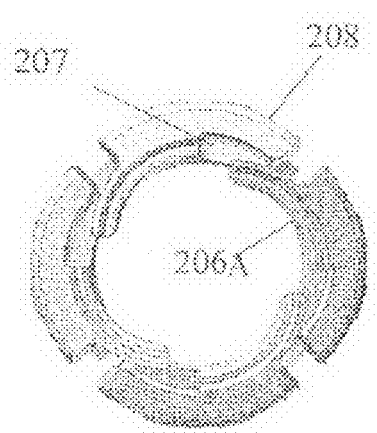
FIG. 31C
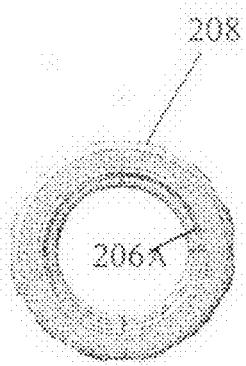
FIG. 31D

ATRAUMATIC CIRCUMCISION APPARATUS AND METHOD OF USING SAME

CROSS REFERENCE TO RELATED APPLICATIONS

The present invention claims benefit of U.S. Provisional Application Ser. No. 61/121,415, entitled "ATRAUMATIC CIRCUMCISION APPARATUS AND METHOD" filed on Dec. 10, 2008, and is a Continuation In Part Application of U.S. Non-Provisional application Ser. No. 11/768,808, entitled "SELF-ADJUSTING PRESSURE APPLICATOR" filed Jun. 26, 2007, which claims benefit of U.S. Provisional Application Ser. No. 60/816,798, entitled "SELF-ADJUSTING PRESSURE APPLICATOR" filed on Jun. 26, 2006, and is a Continuation In Part Application of U.S. Non-Provisional application Ser. No. 11/571,120, entitled "ATRAUMATIC CIRCUMCISION APPARATUS AND METHOD" filed May 14, 2007, which is a 371 of PCT/US05/22404, entitled "ATRAUMATIC CIRCUMCISION APPARATUS AND METHOD" filed Jun. 23, 2005, which claims benefit of U.S. Provisional Application Ser. No. 60/583,259, entitled "ATRAUMATIC CIRCUMCISION RING AND METHOD" filed on Jun. 25, 2004, all are incorporated herein by reference which is incorporated herein by reference.

FIELD OF THE INVENTION

The present invention is related generally to the field of circumcision, and more particularly to a method and device for neonatal circumcision enabling surgical removal of the excess foreskin or prepuce from the neonatal penis by a non-traumatic approach, eliminating the need for the traditional dorsal slit.

BACKGROUND OF THE INVENTION

Newborn circumcision is the most commonly performed surgical procedure in the United States with over 1 million circumcisions performed annually. Circumcisions have been performed for centuries for both religious and medical reasons. Various instruments have been developed to help facilitate removal of the foreskin from the penis. These instruments were intended to provide some level of hemostasis to help control bleeding, to provide a uniform cutting surface, and to protect the underlying glans penis from trauma associated with the procedure. Of these devices, three are commonly used for neonatal circumcision in the United States: U.S. Pat. No. 119,180 ('180) by A. A. Goldstein, U.S. Pat. No. 2,747,576 ('576) by H. Bronstein, and U.S. Pat. No. 2,272,072 ('072) by C J. Ross and U.S. Pat. No. 3,056,407 ('407) by D. H. Kariher et al.

One shortcoming of all the prior art is that a dorsal slit in the foreskin is required. In a neonate, the opening of the foreskin at the tip of the penis is small and tight. A dorsal slit is made to free adhesions or separate the foreskin from the penis, allow enough room to accommodate a cutting surface, and to facilitate alignment of a cutting tool. This procedure causes a traumatic incision to be made on the dorsal surface of the foreskin, perpendicular to and unrelated to the final incision. In order to create the dorsal slit, considerable trauma is exerted to the foreskin and to the neonate.

In order to initiate the dorsal slit, it is necessary to grasp the foreskin. In practice, this is routinely done with two hemostats that are used to clamp and crush the distal foreskin at the ten o'clock position and the two o'clock position. By clamping and therefore crushing the foreskin, the surgeon is able to apply counter traction with one hand holding both instruments, while the surgeon uses the free hand to manipulate a third, straight hemostat to probe under the foreskin and then crush along the dorsal aspect. Scissors are used to cut the dorsal slit where the tissue was crushed. In order to create the dorsal slit, the foreskin of the newborn infant is unnecessarily crushed multiple times and cut.

Studies published by the American Academy of Pediatrics state that a majority of circumcisions are done without any form of anesthesia. The dorsal slit incision accounts for a significant amount of the pain and trauma associated with a circumcision. In addition, the dorsal slit can be a source for significant bleeding and possible infection. Additionally, the Food and Drug Administration (FDA) regularly reports cases where when attempting to perform the dorsal slit the surgeon inadvertently inserts the tip of the scissors into the urethral meatus and cuts not only through the foreskin but the glans penis itself.

The most commonly used neonatal circumcision clamp is described in U.S. Pat. No. 119,180 ('180) by A. A. Goldstein (referred to herein as the Gomco). It consists of a metallic bell that is used to cover the glans or head of the penis to provide protection. After the dorsal slit is made as described above, the foreskin is pulled over the bell and the bell is advanced upward through a hole that serves as a clamping surface. A fulcrum and a screw nut are used to apply a force between the clamp and the bell, which crushes the foreskin and serves to help control bleeding during the incision. One of the shortcomings of the Gomco is the difficulty to pull the foreskin up through the clamp because of the small hole and the size of the clamp. It is a common practice for surgeons using the Gomco to use a common safety pin to pierce the foreskin of the penis on either side of the dorsal slit to hold the foreskin together and to facilitate pulling the foreskin into the clamp. Piercing the foreskin twice with a sharp, large needle generates unnecessary pain and increases the possibility of bleeding and traumatic complications. Yet another shortcoming of the Gomco is that the bell is separate from the clamp making it possible to use the wrong size bell with the wrong size clamp. Traumatic complications, including penile amputations, have been caused because of this mismatch of bell and clamp. Furthermore, it is awkward to manipulate the large clamp and to attempt to pull the foreskin through the small bell opening while engaging the clamping mechanism. Lastly, the final incision is made with the free hand of the surgeon with a conventional scalpel attempting to cut around the bell. This procedure imposes a possibility of inadvertent placement of the scalpel in the wrong position with associated catastrophic outcomes, such as penile amputation.

Another commonly used circumcision device is described in U.S. Pat. No. 2,272,072 by Ross and U.S. Pat. No. 3,056,407 by Kariher et al. (referred to herein as the Plastibell), which also requires the traumatic dorsal slit. The Plastibell employs a plastic bell that is tied off with a string in a form of tourniquet. The remaining foreskin is trimmed with scissors. The plastic handle of the bell is broken off and the plastic bell stays in place until the foreskin necrosis and falls off The most reported complication of the Plastibell is increased infections due to the foreign body nature of the plastic bell, string, and necrotic tissue. Many parents object to this method, because they do not want to have to worry about the plastic bell that stays in place for up to 5 days following the circumcision. Another shortcoming is that the string can be cut inadvertently by the surgeon performing the circumcision causing excessive bleeding. The string can also be tied with insufficient applied pressure to prevent bleeding. As with the Gomco, the chance for damage to the urethral opening of the glans is possible because the surgeon makes the incision with scissors. Lastly, it is very difficult and awkward to simultaneously hold the plastic bell in place, keep the foreskin together, and tie a knot in the string at the precise location on the plastic bell.

Yet another circumcision device is described in U.S. Pat. No. 2,747,576 ('576) by H. Bronstein (referred to herein as the Mogen clamp). The Mogan clamp is used less frequently because it is difficult to ensure that excessive foreskin or the head of the penis has not been inadvertently pulled up into the clamp. If the head of the penis is inadvertently pulled up into the clamp, the resulting clamping and incision causes an amputation of the tip of the penis. The FDA has issued several warnings regarding this shortcoming of the Mogen clamp. Furthermore, the cosmetic outcome is often that the remaining foreskin is lopsided and asymmetric because the incision is made in a linear direction and the underlying tissue has a circumferential orientation.

In August of 2000, the FDA released a cautionary statement regarding the Gomco and Mogen type clamps. The FDA reported receiving 105 reports of injuries involving circumcision clamps between the months of July 1996 and January 2000 or approximately 30 injuries per year. Assuming a similar injury rate for the preceding 54 years, when these devices were initially introduced, they have likely accounted for well over 1600 traumatic outcomes. Those incidents reported by the FDA included lacerations, hemorrhages, penile amputations, and urethral damage.

U.S. Pat. No. 3,072,126 by P. M. Fenton ('126) discloses the use of an axial circular cutting means to apply hemostasis compression to the foreskin as well as to cut the foreskin. The axial compression force applied by the circular cutting means to crush the foreskin invariably stretches and deforms the foreskin. As the circular cutting means is engaged, the foreskin is frequently and inappropriately pushed down over the bell or tube making it difficult to predict the length of foreskin to be removed. Since the same surface is used to cut the foreskin as well as to create the hemostatic crush to the foreskin, it would be difficult to ensure that the foreskin is not inadvertently cut prior to the application of enough compressive pressure to achieve hemostasis leaving the possibility of dangerous bleeding complications. Further, '126 requires use of a bell or tube to shield the glans, necessitating the inherent need for a dorsal slit to be made in the foreskin to facilitate the placement of the foreskin on to the bell or tube.

U.S. Pat. No. 3,473,533 by J. C. Freda ('533) discloses the use of an axial circular cutting means to cut the foreskin after an axially applied force creates a compressive force for hemostasis. The axial compression force to crush the foreskin invariably stretches and deforms the foreskin as the clamping member is applied. As the clamping member is engaged, the foreskin is frequently inappropriately pushed down over the bell or tube making it difficult to predict the length of foreskin to be removed. The incision to the foreskin is made independent of the crush which leaves open the dangerous possibility that an operator can inadvertently administer the cut without having first clamped the foreskin to create hemostasis. Further, '533 requires use of a bell or tube to shield the glans, necessitating the inherent need for a dorsal slit to be made in the foreskin to facilitate the placement of the foreskin on to the bell or tube.

A particular shortcoming shared by the prior art references is that none disclose a means to prevent the possibility of mismatched parts. The possibility of mismatched equipment or the use of a small shield with a large clamp has caused dangerous catastrophic outcomes as regularly reported by the FDA. These injuries are severe and include lacerations and penile amputations.

SUMMARY OF THE INVENTION

The present invention generally includes two cooperating components: a ring component and a clamping-cutting device. One embodiment of the ring component includes an open circular ring mounted to one end of a shaft. One embodiment of the clamping-cutting device includes a plurality of retractable arms operably connected to at least one movable lever arm. The clamping-cutting device also includes a cutting device (such as a circular blade) disposed within the clamping-cutting device, which is also operably connected to a lever arm. The shaft of the ring component may include a notch in a predetermined location to engage the clamping-cutting device to ensure precise positioning of the clamping-cutting device in relation to the open circular ring. The open circular ring may also include a circumferential groove along the outer surface of the open circular ring adapted to receive the edges of the retractable arms.

In operation, the ring component is manipulated between the foreskin and the penis and positioned just above the glans of the penis. The open ring allows insertion of the ring component into the foreskin without making a dorsal slit. This provides the placement of a clamping and cutting surface within the foreskin without making the unnecessary and traumatic dorsal slit. Once the open ring is placed within the foreskin without making a dorsal slit, the clamping-cutting device is placed onto the shaft of the ring component. The clamping-cutting device is then activated by moving the lever arm from the open to closed position. As the lever arm is moved downward or toward the closed position, the clamping-cutting device is moved over the plurality of retractable arms causing the arms to move radially inward to the closed position exerting a lateral, symmetric clamping force to the ring that serves to crush the foreskin. By exerting a lateral, symmetrical force, no manipulation or deformation of the foreskin has to occur to get it into the clamp. The ring is positioned within the foreskin and remains in that location until the lateral clamping force is applied. There is no need to pull or manipulate the foreskin to get it into the clamp. The clamp is delivered laterally and symmetrically to the foreskin and ring so there is no deformation to the foreskin prior to it being crushed, ensuring a more precise, reproducible, and predictable circumcision. In the closed position, the plurality of retractable arms close on to and engage the open circular ring, thereby closing the ring and crushing or clamping the foreskin against the now closed circular ring. At the moment the crush occurs, the foreskin remains in its anatomically correct position, improving the likelihood the physician can accurately determine the correct amount of foreskin to remove. Continued movement of the lever arm advances the cutting device towards the circular ring that cuts the foreskin clamped between the retractable arms and the circular ring.

One aspect of the present invention adapts a cutting device (such as a blade) to an actuator such that the cutting device translates parallel with the shaft of the penis when cutting the foreskin. The mechanical actuation of the cutting device provides an improvement in the control of the position of the cutting device relative to the shaft of the penis. The cutting device preferably translates along the common axis of the actuator which in turn translates along the common axis of the shaft of the ring component. The shaft of the ring component facilitates translation of the clamping-cutting device along the common axis providing control of the positioning and alignment of the cutting device with the compression and cutting surface of the ring component. The position of the shaft in relation to the compression and cutting surface is fixed such that the cutting device can only reach the exact location of the cutting surface, protecting surrounding tissue and eliminating any chance of inadvertent damage to the penis from the cutting blade. The blade is an integral part of the device, the incision can not be made until the housing has closed the retractable arms ensuring adequate clamping and crushing. The path of the blade is precisely controlled by the device itself, not the operator, ensuring the incision is made in the precise location, independent of the operator. The design of the present invention essentially eliminates the possibility of making an incision without having adequately crushed the foreskin. With this device, the timing of the crush and cut is precisely controlled, the incision can not occur without first crushing the foreskin.

Another aspect of the present invention is that the blade is contained and protected within the device itself, essentially eliminating the chance of inadvertent trauma to surrounding structures.

Another aspect of the present invention is that the internal shape of the opening of the clamping-cutting device can be made such that it can only mate with an appropriate ring. Anatomic variation requires devices of different size. This requires different size housings and different size rings. In order to completely eliminate the chance of using mismatched parts, the housing and ring will be uniquely mated, so that only the exact housing can be used with a particular sized ring. This mechanical specification will eliminate any chance of a user inadvertently using the wrong size ring with the wrong size clamping-cutting device. The design of this invention eliminates the possibility of mismatched parts and their potential catastrophic outcomes.

Another aspect of the present invention is that the open ring can be made to interact with the clamping-cutting device such that a mechanical stop can be used to control when and how the levers are activated. By using a mechanical stop, the two parts can be designed such that the lever arms can not be activated unless the clamping-cutting device is positioned in the exact position on the ring that inhibits the mechanical stop. This type of interaction can ensure that the clamping-cutting device can only be placed on the ring when in the open position, and the lever arms can only be activated when the clamping-cutting device is in the exact position on the ring. Furthermore, the design makes it impossible to move the housing once the lever arms have been activated, eliminating the chance of the operator pulling off the housing prior to completion of the crushing and the incision. The design ensures that the only way the operator can put the clamping-cutting device on the shaft of the ring is in the open position, eliminating the chance of the operator erroneously putting the clamping-cutting device on in the closed position. Furthermore, the design eliminates the chance of the operator activating the lever arms before the clamping-cutting device is in the exact location. It can also eliminate the chance of the clamping-cutting device moving at all along the shaft once the lever arms have been activated. The mechanical control of these important procedural elements ensures a reproducible, risk free circumcision, independent of the operator.

Other embodiments of the invention include a closed ring, tongue and groove clamp arm members, housing extension, lever arm locking mechanism, visual ring engagement indicator, slip gear and safety mechanism.

It is an object of the present invention to provide a device to easily perform newborn circumcision, shorten the operation time, produce reliable and consistent outcomes, and substantially eliminate the risk of human error and catastrophic outcomes.

It is a further object of the present invention to provide a device to perform neonatal circumcision that eliminates the need for the traditional dorsal crush and slit, thereby minimizing bleeding and significantly reducing the trauma and pain associated with the procedure.

It is a further object of the present invention to provide a device that delivers a lateral, symmetrical clamping force to the foreskin and the ring thereby eliminating the need to pull or manipulate the foreskin to position it in the clamping means.

It is a further object of the present invention to provide a device that facilitates the use of a circular cutting device that is delivered longitudinally to the shaft of the penis and performs a single circumferential and uniform incision.

It is a further object of the present invention to provide a device that integrates and encloses the circular blade within the device such that the device itself provides precise control over the delivery of the cutting surface while protecting the patient and user from inadvertent injury, essentially eliminating the chance of user error and catastrophic complications.

It is a further object of the present invention to provide a device that adapts a mechanical means to control the crushing of the foreskin and the delivery of the blade, ensuring that the incision can only be made after the foreskin has been sufficiently crushed.

It is a further object of the present invention to provide a mechanical means that completely eliminates the chance of mismatching different sized parts, eliminating the chance of a ring component being used with the wrong sized crushing-cutting device.

It is a further object of the present invention to use a lever arm with semicircular gears and a gear track to activate device.

It is a further object of the present invention to have the ability to manufacture each of the non-cutting surface parts out of plastic materials allowing the device to be disposable or recyclable for one time use, eliminating the need for autoclaving, reducing the risk of mismatched parts, and reducing the risks associated with using worn or damaged parts.

It is a further object of the present invention for the various sized parts to be made in differing colors based on size to assist users in identifying appropriate parts and appropriate sizes, expediting the procedure, and further avoiding the chance of mismatched parts.

It is a further object of the present invention to incorporate a mechanical means or lever locking system that ensures the levers that activate the device can only be activated when precise alignment of the ring and the clamping-cutting device has been achieved. And such mechanical means ensures the position of ring and clamping-cutting device is maintained throughout the actuation of the device.

It is a further object of the present invention to generate an audible sound when the lever arms have been successfully actuated to inform the operator that the crushing and cutting actions have been completed.

For a better understanding of the present invention, together with other and further objects thereof, reference is made to the accompanying drawings and detailed description.

BRIEF DESCRIPTION OF THE DRAWINGS

The present invention is illustratively shown and described in reference to the accompanying drawings, in which:

FIGS. 10, 11, and 12 are cross sectional views of various embodiments of the present invention illustrating insertion of various sized clamp-cutting surface apparatus into a clamping-cutting device;

FIGS. 13 and 14 are pictorial views of an alternative embodiment of the present invention;

FIG. 19 is a cross section view of yet another alternative embodiment of the present invention;

FIG. 20 is an exploded view of the alternative embodiment of FIG. 19.

FIGS. 23A-B are side views of the foreskin holder of FIG. 22;

FIG. 23C is a bottom view of the foreskin holder of FIG. 22;

FIG. 31A illustrates a cross section of the foreskin being held in position by the present invention prior to clamping and cutting by the clamping-cutting device of FIG. 30;

FIG. 31B illustrates a cross section in the crushing and cutting position.

FIG. 31C demonstrates a bottom view of just the retractable arms in the open, neutral, pre-clamping position.

FIG. 31D demonstrates a bottom view of just the retractable arms in the closed, clamping position.

DETAILED DESCRIPTION OF THE INVENTION

Figure 1:
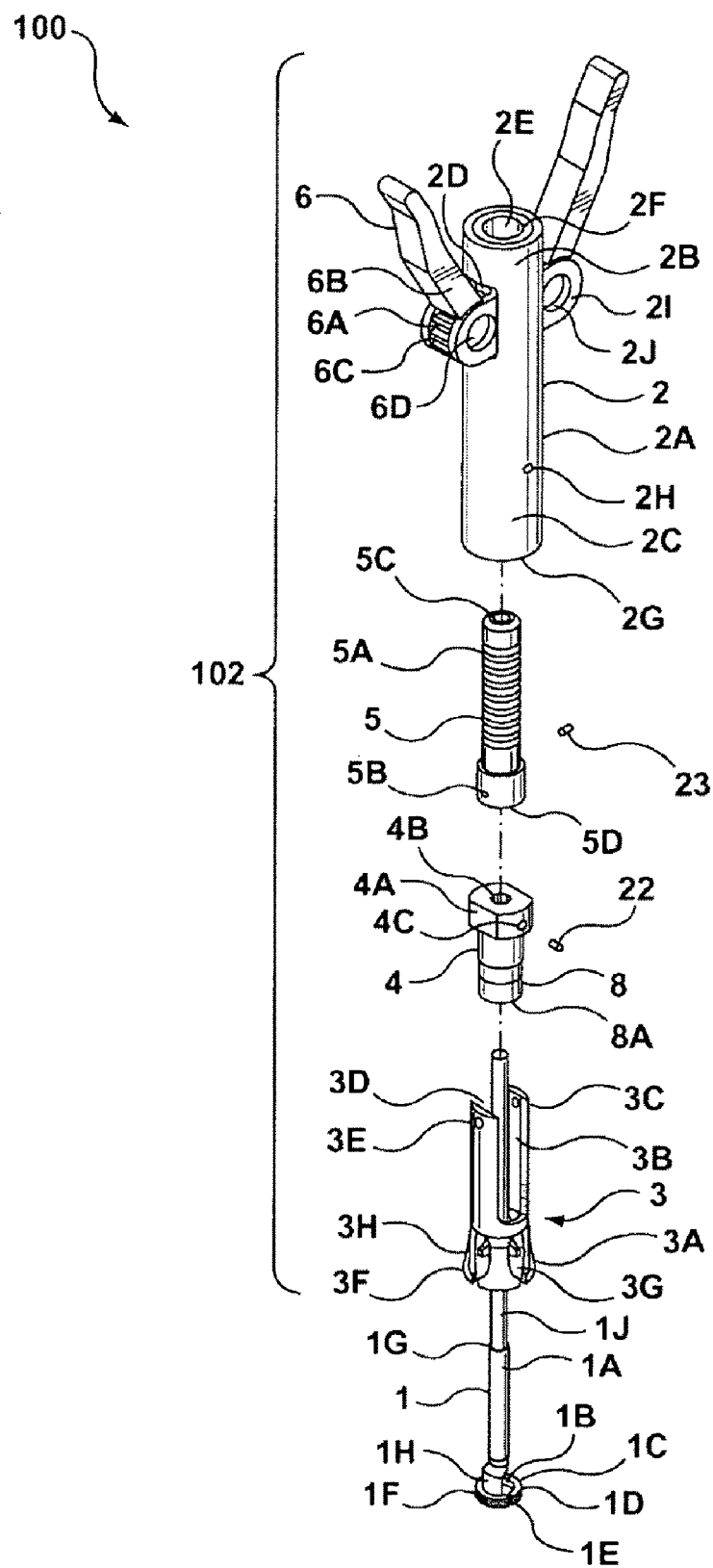
FIG. 1 is an exploded view of the present invention.
Figure 2:
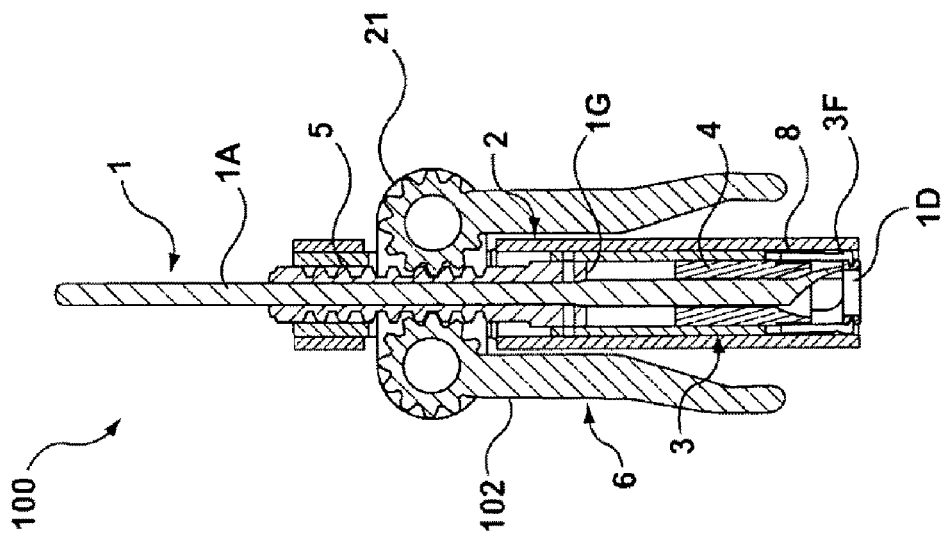
FIG. 2 is a cross-section of the present invention of FIG. 1 in the opened or relaxed position.
Figure 3:
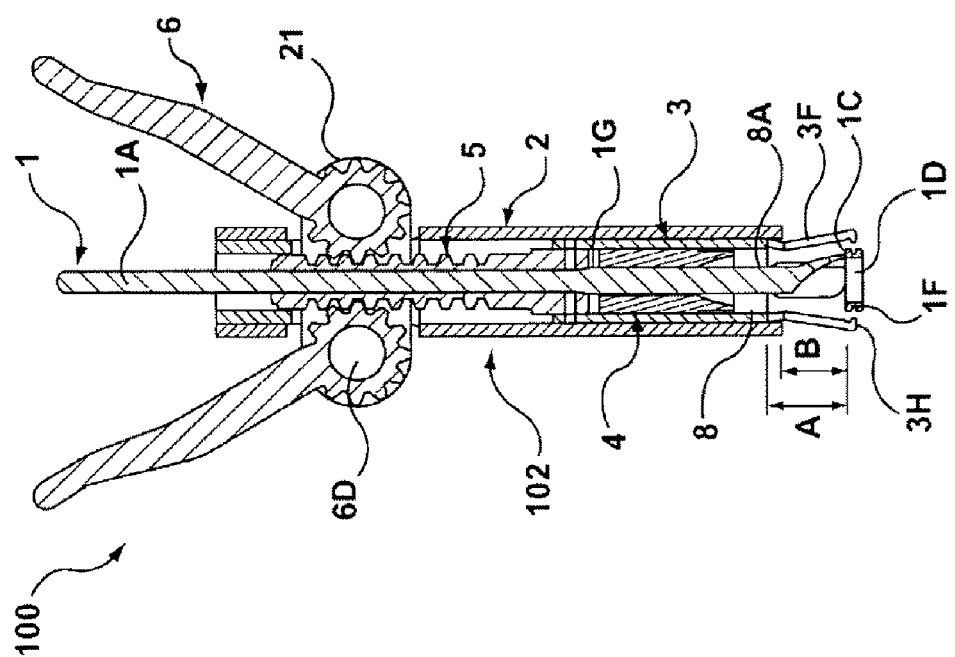
FIG. 3 is a cross-section of the present invention of FIG. 1 in the closed or engaged position.

One aspect of the present invention 100, illustrated in FIGS. 1, 2, and 3, includes ring component 1 and clamping-cutting device 102. Clamping-cutting device 102 includes operably connected housing 2, clamping member 3 with retractable arms 3F, blade holder 4 with integral blade 8, gear track 5, and two lever arms 6. Clamping member 3 is operably connected to lever arms 6 such that when lever arms 6 are actuated up retractable arms 3F are positioned out of clamping-cutting device 102 to the opened or resting position (FIG. 2) or when lever arms 6 are actuated down the clamping-cutting device 102 traverses over the clamping member 3 to the closed or engaged position (FIG. 3).

In the open position (FIG. 2), the ring component 1 is free to move into and out of clamping-cutting device 102. As lever arms 6 move downward to the closed position (FIG. 3), retractable arms 3F of clamping member 3 radially close and apply substantially even circumferential pressure to open ring ID of the ring component 1 to firmly close the ring ID and hold the ring component 1 in place as the housing 2 of the clamping-cutting surface 102 is advanced over the retractable arms 3F. In the clamped configuration, the ring component 1 and the clamping-cutting device 102 act as a single, integral component controlled by the actuation of level arms 6. Downward progress of crushing-cutting component 102, a distance designated B, advances housing 2 over retractable arms 3F such that the clamping operation is fully activated or engaged. At the moment the housing 2 has been advanced the distance B and the crush has been completed, the blade has traveled the same distance B and is positioned above the ring and cutting surface. It is not until the lever arm 6 has been further actuated and the housing 2 and blade 8 have been advanced further down clamping member 3 a distance designated A that the cutting edge 8A is brought into contact with the cutting surface 1C of ring ID thereby incising the foreskin positioned between the cutting edge 8A and the cutting surface 1C. During further advancement of housing 2 over the retractable arms the crushing force of retractable arms 3F are maintained by the inner diameter of the housing 2. The timing of the crush and cut is controlled by distances A and B. These distances are sufficiently different to ensure that the clamping action occurs prior to the incision. And more importantly, that an incision can not possibly be made without first activating and maintaining the clamping action. Downward progress A of crushing-cutting component 102 stops when the cutting edge 8A of blade 8 contacts the top or cutting surface 1C of ring ID of the ring component 1. The sequence of the crush and cut is controlled by the device itself when the operator actuates the lever arms downward fully in one single motion. As lever arms 6 are actuated, the present invention clamps the foreskin radially to create a substantially symmetrical and even circumferential hemostasis at the axial position and at the same time as the motion continues and only after the crush has occurred, delivers the cutting edge of blade 8 to the cutting surface 1C of the ring ID completing the incision slightly above where the clamping member 3 crushed the foreskin and achieved the hemostasis effect. The incision to the foreskin is made while the foreskin is within housing 2 and can be out of the direct line of sight of the operator if housing 2 is made of a non-transparent material or colored.

Housing 2 is generally cylindrical, hollow, and vertically longitudinal having a top portion 2B and a bottom portion 2C. Housing 2 includes top portion 2B, bottom portion 2C, opposing slots 2D, through bore 2E, top opening 2F, bottom opening 2G, assembly hole 2H, and two pairs of projections 21. Bore 2E includes a sufficiently sized inner surface and length to receive therein clamping member 3, blade holder 4, gear track 5, and ring component 1.

Two lever arms 6 are pivotally joined to top portion 2B about a pivotal axis. Each lever arm 6 has a predetermined length and width sufficient to sustain the forces of clamping and cutting. Semi-circular gears 6A are adapted to the distal end 6B of each lever arm 6 and a handle at the other end. Lever arms 6 are positioned on opposite sides of top portion 2B of housing 2 and positioned such that a portion of semi-circular gear 6A extends through a slot 2D in housing 2 so as to engage gear track 5 within housing 2. Each semi-circular gear 6A includes a plurality of gear teeth 6C. Width of lever arms 6 are sized to fit between pair of projections 21 and are pivotally attached to projections 21 by a conventional joining device (not shown) such as bolt/nut or bushing or pressed fit pin connection. Each projection 21 may include hole 2J to receive the conventional joining device. Each semi-circular gear 6A may include a through bore 6D to receive the conventional joining means there through pivotally connecting each lever arm 6 and projection 21 with one conventional joining means. Alternatively, two conventional joining means can be inserted through each projection 21 into semi-circular gears 6A, either with or without a through bore, to form the pivotal connection. Projections 21 act as a pivotal axis for lever arms 6 and allow lever arms 6 to rotate or pivot about an axis. Pivotal movement of lever arms 6 causes rotation of semi-circular gears 6A to impart reciprocating movement to gear track 5. Semi-circular gears 6A have a diameter that is sufficient to linearly move housing 2 up and down over retractable arms 3F.

Bottom opening 2G of bottom portion 2C of housing 2 has an inside diameter that is made to accommodate the top portion of clamping member 3. As housing 2 is advanced down over clamping member 3, the inside diameter of housing 2 causes retractable arms 3F of clamping member 3 to radially close, such that when housing 2 is advance completely over clamping member 3, retractable arms 3F are closed and in a position to engage open ring ID and exert a significant compressive force on grooved outer surface IF of open ring ID.

Gear track 5 includes a plurality of gear teeth 5A evenly spaced along the length of gear track 5. Gear track 5 further includes through radial hole 5B for connecting clamping member 3 to gear track 5 (disclosed in detail below). Gear track 5 is initially positioned within top portion 2B of housing 2 and is capable of axial movement within housing 2 in either longitudinal direction. Gear teeth 5 A of gear track 5 cooperate with gear teeth 6C of semi-circular gears 6A to translate gear track 5 axially within bore 2E of housing 2. Gear track 5 has a vertical passageway 5C extending through its axial center that is sized to receive only the narrow portion of shaft IA of ring component 1. By accommodating only the narrow part of shaft IA, bottom face 5D contacts or rests on notch, ledge or shoulder IG of shaft IA, and therefore aligns the clamping-cutting device 102 with ring component 1 and open ring ID (discussed in detail below). Shoulder IG can be formed by shaft IA having two sections with different diameters: an upper section IJ having a diameter smaller than diameter of 5C and a lower section IA having a diameter larger than diameter of 5C. Gear track 5 is freely rotatable about its axis and gear teeth 5A extend circumferentially around gear track 5. The contact at any given time between gear teeth 6C of semi-circular gear 6A and gear teeth 5A on gear track 5 is limited to a single tooth and preferably a single point contact.

Blade holder 4 includes circular blade 8 and blade support 4A. Circular blade 8 and blade support 4A are connected by conventional means including, for example, snap fit, press or interference fit, cooperating male/female threaded members, screw, bolt, pin, weld, or adhesive. Blade support 4A includes longitudinal through bore 4B (disclosed in detail below). Blade support 4A may include retention hole 4C to connect blade holder 4 to housing 2 with, for example pin 22. Further, blade holder 4 has an outer diameter less then that of the inside diameter of clamping member 3 such that blade holder 4 can move freely longitudinally within clamping member 3. At the location of slot 3D in clamping member 3, blade holder 4 is affixed to housing 2 and moves simultaneously with housing 2. Blade holder 4 and housing 2 are attached together and move as one component. The attachment point occurs at the location of slot 3D such that housing 2 and blade holder 4 can move independently of clamping member 3.

Clamping member 3 is generally a hollow cylindrical member with lower end 3A and upper end 3C. Clamping member 3 is freely moveable within the lower part of housing 2. The hollow center of clamping member 3 allows for the positioning and passing therethrough of blade holder 4. Clamping member 3 includes a plurality of retractable arms 3F at lower end 3A. Upper end 3C is defined by two extensions 3B positioned on opposite sides of the cylinder at upper end 3C. Pair of extensions 3B are adapted to form slot 3D. Slot 3D is sized to receive blade holder 4 and gear track 5. Each extension 3B includes retention hole 3E for connecting clamping member 3 to gear track 5 with, for example, pin 23. Slot 3D extends longitudinally along the cylinder and allows for fixation of blade holder 4 to housing 2 (discussed in detail below) without interfering with clamping member 3 ability to traverse within housing 2. Once clamping member 3 is fixedly attached to gear track 5, gear track 5 drives housing 2 up and down over clamping member 3, thereby opening and closing retractable arms 3F.

As discussed above, lower end 3A of clamping member 3 includes a plurality of circumferentially evenly spaced, downwardly facing, outwardly tapered, flexible retractable arms 3F. Retractable arms 3F can be made of elastic material, such as plastic, metal, graphite, or other polymer, that retains its spring-like characteristics. The ends of retractable arms 3F form an opening 3G adapted to engage grooved outer surface IF of open ring ID. When the present invention is in the opened or relaxed position, opening 3G is larger then the outer diameter of open ring ID. Retractable arms 3F extend outwardly in a tapered manner allowing for an open position that allows for positioning of clamping member 3 over the outside diameter of the upper section IJ of shaft IA. As housing 2 is advanced down over retractable arms 3F, the inside diameter of housing 2 engages the tapered edge of retractable arms 3F and results in the closure of retractable arms 3F. When retractable arms 3F are closed, the ends of retractable arms 3F define an opening 3G that is substantially the same diameter as the outer diameter of open ring ID when gap IE of open ring ID is closed. Retractable arms 3F, when closed, cooperate with grooved outer surface IF of open ring ID to crush the foreskin for a hemostasis effect and hold open ring ID in a secure, fixed position prior to the delivery of the axial force of blade 8 to the prepuce foreskin.

As discussed above, retractable arms 3F are fully extended or opened in the unrestrained condition, thereby forming the largest opening diameter 3 G possible. As retractable arms 3F are drawn axially into, for example, housing 2, retractable arms 3F move radially inward, thereby reducing the diameter of opening 3G. Retractable arms 3F are adapted to engaged ring component 1, crush the foreskin, and restrain the movement of ring component 1. Each retractable arm 3F may include inward radial extension 3H, which is preferably curved to fit the contour of grooved outer surface IF, to further enhance the hemostasis effect. Four retractable arms are illustrated, however, any number of arms are acceptable that achieve the desired results discussed in detail below.

One embodiment of the clamping-cutting device 102 can be assembled by aligning retention hole 3E of clamping member 3 with radial hole 5B of gear track 5. A conventional means such as a screw, bolt, or press-fit pin 23 is inserted through retention hole 3E and radial hole 5B of gear track 5, thereby connecting together clamping member 3 and gear track 5. Blade holder 4 is placed within the assembled clamping member 3/gear track 5 and the entire assembly is positioned within through bore 2E of housing 2. Retention hole 4C of blade holder 4 is aligned with assembly hole 2H of housing 2. A conventional means such as a screw, bolt, or press-fit pin 22 is inserted through retention hole 4C of blade holder 4 and assembly hole 2H of housing 2, thereby connecting together housing 2 and blade holder 4. Each lever arm 6 is positioned between pair of projections 21. Semi-circular gears 6A are extended into housing 2A through slot 2D. Gear teeth 6C of semi-circular gears 6A are positioned to engage gears 5A of gear track 5. A conventional joining device is adapted to pivotally attach lever arm 6 to projection 21, thereby completing the assembly of clamping-cutting device 102.

Figure 4:
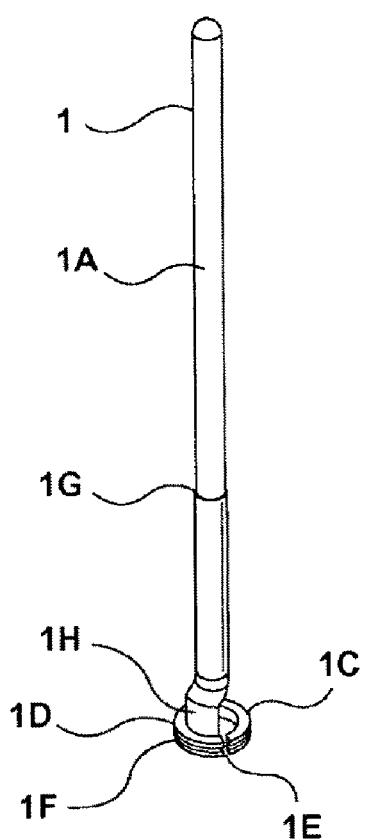
FIG. 4 is a pictorial view of one embodiment of the clamping-cutting surface apparatus of the present invention.
Figure 5:
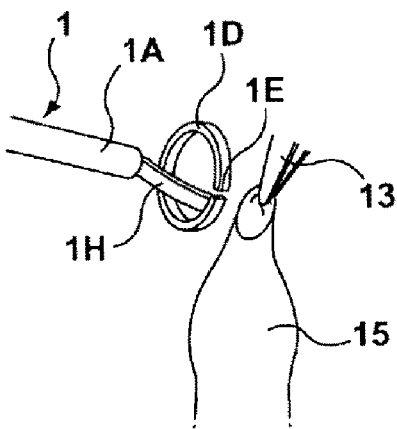
FIGS. 5, 6, 7, and 8 are pictorial views of the clamp-cutting apparatus being inserted into the foreskin of the neonatal penis.
Figure 6:
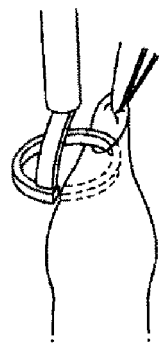
Figure 7:
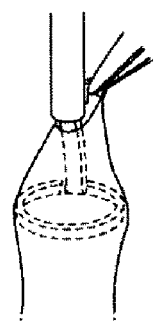
Figure 8:
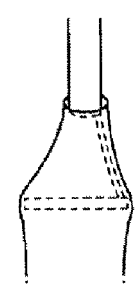

Now turning to FIG. 4, ring component 1 is generally a single piece of malleable, elastic material (such as plastic) with an open ring ID mounted orthogonally to shaft IA by curved member IH, which allows manipulation of open ring ID within the foreskin. Shaft IA includes a plurality of diameters to control the insertion of ring component 1 into clamping-cutting device 102. A shaft diameter change can be delineated by a notch or ledge or, as illustrated in FIG. 1, shoulder IG that acts as a stop of ring component 1 into clamping-cutting device 102. Open ring ID includes a cutting surface 1C on its top surface being adapted to act as a cutting surface when cutting edge 8A of blade 8 is pressed down against foreskin interposed between cutting surface 1C and cutting edge 8A. Open ring ID may also include grooved outer surface IF adapted to engage with inward radial extension 3H of retractable arm 3F to hold ring component in a stationary position relative to housing 2 during the clamping/cutting operation, such that the foreskin is trapped between the grooved outer surface IF and the retractable arms 3F. Further, grooved outer surface IF will interact with inward radial extension 3H to crush the foreskin against open ring ID and contemporaneously hold ring component 1 in position while circular blade 8 is delivered to make the incision in the foreskin. Open ring ID includes an opening or gap IE large enough to allow the thickness of the foreskin to enter. The inner diameter of the open ring ID is large enough to receive a predetermined sized glans and shield the glans or head of the penis from being clamped and/or cut.

FIGS. 5, 6, 7, and 8 demonstrate the insertion of open ring ID into the neonatal foreskin 15. As discussed above, opening IE allows entry of open ring ID into foreskin 15. Foreskin 15 is held by an atraumatic forceps 13 while opening IE is positioned to enter foreskin 15. With a pair of non-traumatic forceps, the foreskin is gently grasped and foreskin 15 is guided into the narrow gap IE of open ring ID. With a screw-like motion of shaft IA of ring component 1, the open edge of open ring ID is advanced in, down, and around the inner aspect of the foreskin. The opening or gap IE in open ring ID allows the open edge to be advanced into the foreskin with a smooth, non traumatic fluid screwing motion. Once open ring ID is fully inserted and resides just beneath foreskin 15, it can be pushed down slowly toward the glans to free any adhesions. Inside foreskin 15, opening or gap IE is closed by the elastic nature of the foreskin. The closed open ring ID, inside the foreskin of the penis, residing just above the glans or tip of the penis, is then used as the compressive surface for any number of clamps, such as inward radial extension 3H, and its top surface acts as a combination glans shield and or cut surface for blade 8 as it cuts the foreskin.

Figure 9:
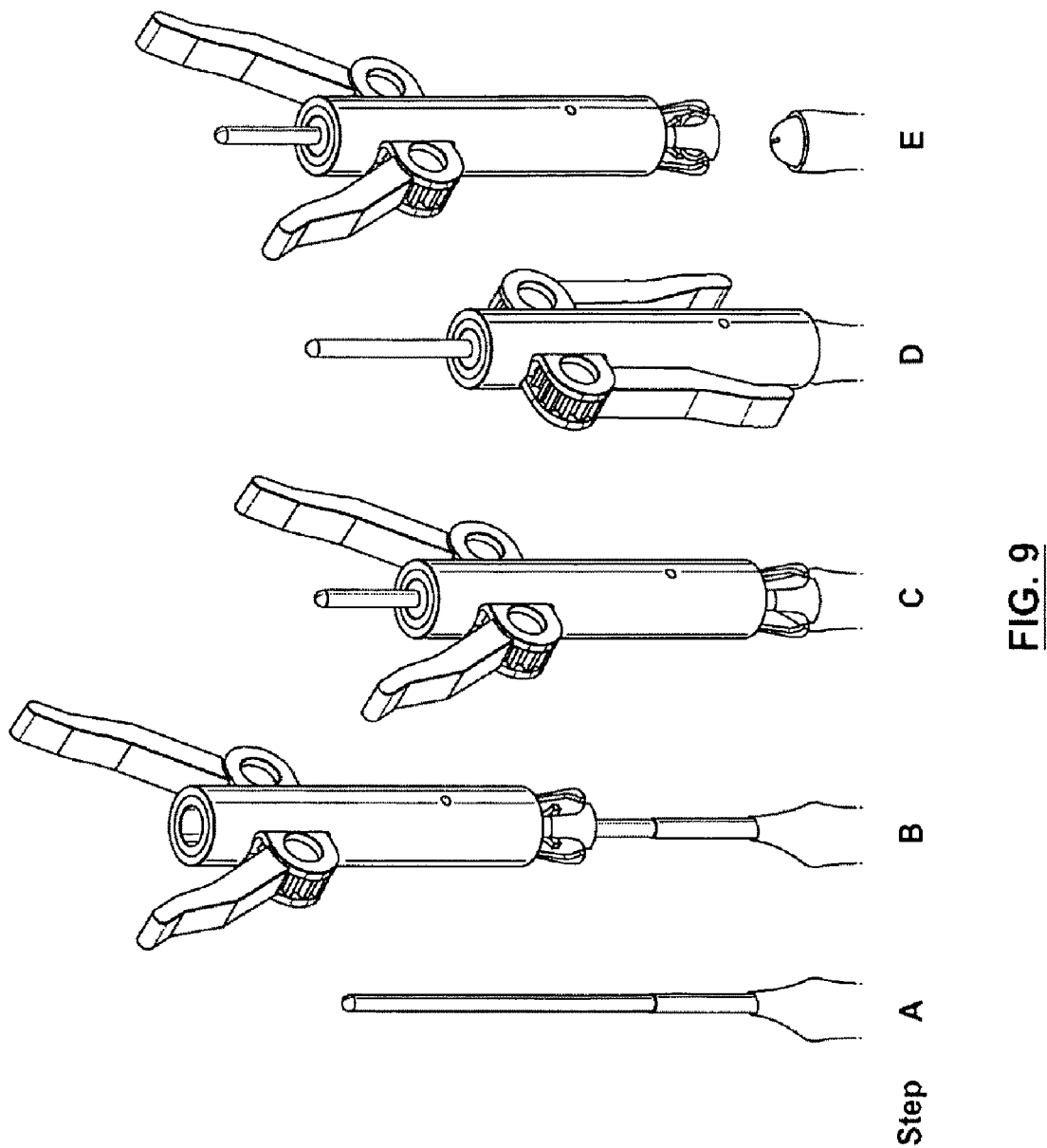
FIG. 9 are pictorial views illustrating use of the present invention.

FIG. 9 illustrates the method of using the present invention to perform a neonatal circumcision. Step A: Open ring ID of ring component 1 is inserted into the foreskin of the penis, as discussed above. Step B: Clamping-cutting device 102 is set in the open position with lever arms 6 rotated up and retractable arms 3F extending fully through the bottom of housing 2. Step C: Clamping-cutting device 102 is inserted onto shaft IA of ring component 1. Downward movement of clamping-cutting device 102 and housing 2 onto shaft IA is stopped when shoulder IG contacts bottom face 5D of gear track. Step D: Lever arms 6 are activated downward to advance housing 2 downward over retractable arms 3F causing the clamping force and delivering the circular blade to the foreskin. More specifically, semi-circular gears 6A of lever arms 6 engage with gear teeth 5A of gear track 5 of clamping-cutting device 102. Housing 2 moves downwardly over retractable arms 3F causing retractable arms 3F to radially close on to and to exert lateral compressive force against the foreskin. Retractable arms 3F exert sufficient lateral compressive force such that inward radial extensions 3H of retractable arms 3F forces the foreskin into grooved outer surface IF of open ring ID, thereby clamping the foreskin without any trauma or deformation between the ring component 1 and the clamping-cutting device 102. As housing 2 is advanced even further over the open ring ID, blade 8 is delivered to the top surface of open ring ID and creates the circular incision into the foreskin when open ring ID is within housing 2. Using the top surface 1C of open ring ID as the cutting surface that is held in place by the closed retractable arms 3F, blade 8 makes a single, clean, circumferential incision on top of the ring, removing the excess foreskin. The clamp is left in place for a period of time ensuring adequate crushing and hemostasis. Step E: Lever arms 6 are lifted upward and retractable arms 3F release ring component 1, lifting housing 2 of the clamping-cutting device 102 and lifting blade 8 back up into housing 2 and releasing open ring ID. Shaft IA with severed foreskin is removed from housing 2. All components of the present invention and byproducts of the operation are thrown away, thereby completing the circumcision.

FIGS. 10, 11, and 12 illustrate how the present invention eliminates the chance of mismatched parts. In FIG. 10, smaller ring component 16 is shown inside larger housing 17. The location of the shoulder 10 on the shaft of ring component 16 prevents shaft from being inserted all the way into the housing 17. With open ring extending below retractable arms, clamping-cutting surface apparatus 16 and housing 17 are not engaged and blade may not cut foreskin. Therefore, the use of a smaller ring component 16 with larger housing 17 is prevented.

FIG. 11 illustrates a proper fit between ring component 18 and housing 17. Ring component 18 is the appropriate size for the housing 17 and the retractable arms 9 are perfectly aligned with the open ring 14. Ring component 18 and housing 17 engage and blade cuts foreskin.

FIG. 12 illustrates how a larger ring component 19 interacts with a smaller housing 17. In this case, it is the diameter of the shaft of ring component 19 that prevents the shaft from being inserted into housing 17. On the shaft of ring component 19, the location of the shoulder and the diameter of the shaft make up two variables that are used together to completely eliminate the chance that a wrong size ring component could be used with a wrong size housing. Colored coded rings that match the appropriate size housing can be used to help users identify appropriate parts and appropriate sizes.

FIGS. 13 and 14 illustrate an alternative embodiment of the clamping-cutting device of the present invention having a lever-locking system to ensure more accurate deployment of lever arms 6. Lever arm 6 is in the up or open position aligning slot 21 in the pivotal axial shaft of the lever arm 6 that would allow lever arm 6 to be slid into position on the shaft 1. Because of slot 21, lever arm 6, in the position shown, can not be deployed. Lever arm 6 is jammed or blocked from rotating because of the shaft.

In FIG. 14, lever arm 6 has been moved down shaft 1 and is aligned with curved notch 20 in shaft 1. Curved notch 20 allows lever arm 6 to rotate to the down or closed position. The location of curved notch 21 in shaft 1 ensures that lever arms 6 can only be deployed when the clamping-cutting device 2 is in the precise location on shaft 1. Furthermore, once lever arm 6 is deployed, lever arm 6 can not move up or down on shaft 1 because it becomes locked in place as a result of the curved notch 21.

Figures 15, 16:
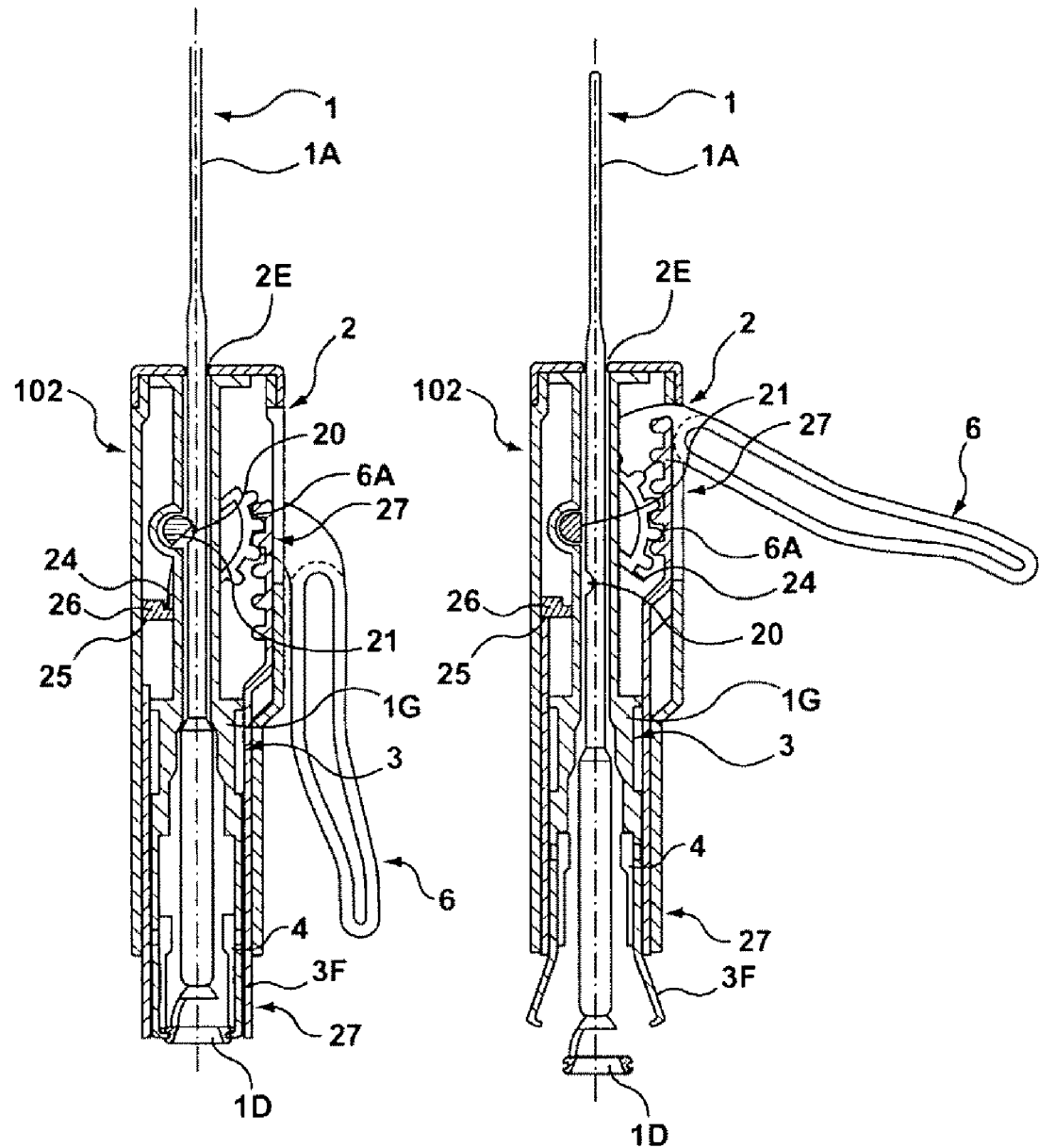
FIGS. 15 and 16 are cross section views of another alternative embodiment of the present invention.

FIGS. 15 and 16 illustrate yet another alternative embodiment of the clamping-cutting device of the present invention in the open and closed position. This embodiment incorporates a means to generate a clicking sound when the lever arm has moved a sufficient distance to ensure clamping and cutting. Elastic projection 24 of semicircular gear 6A makes contact with projection 25 of the clamping member 3. As the semicircular gear 6A rotates, elastic projection 24 is held by projection 25 until semicircular gear 6A rotates a sufficient amount that elastic projection 24 snaps free thereby striking surface 26 of the clamping member and making a distinct click. The position of the elastic projection 24 on the semicircular gear 6A is such that the clicking sound occurs when the lever arm 6 is in the fully closed or down position. The clicking sound provides an audible signal to the operator that the lever arm has been appropriately deployed and that the crushing and cutting is complete.

FIGS. 15 and 16 also demonstrate a clamping-cutting device that has a housing 2 that is fixed to clamping member 3. Once in position on ring component 1, the housing 2 of the clamping-cutting device 102 does not move. Activation of lever arm 6 and semicircular gears 6A causes rotation about an axis fixed to housing 2. Rotation of the semicircular gears 6A activates reciprocating movement of an internal cylindrical sleeve 27 that moves within housing 2 and can be advanced over the clamping member 3 to close retractable arms 3F. The internal sleeve 27 is fixedly attached to blade holder 4 allowing advancement of the sleeve 27 to deliver the blade holder 4 and the cutting surface to ring ID of ring component 1. FIG. 16 demonstrates sleeve 27 and blade holder 4 in the up position, retracted into housing 2. FIG. 15 demonstrates sleeve 27 and blade holder 4 in the down position, extending below housing 2, closing retractable arms 3F and delivering the cutting surface to the top surface of the ring ID.

FIG. 16 also demonstrates a clamping-cutting device that utilizes just one lever arm and demonstrates how the lever-locking system can be used. As shown if FIG. 16, the shaft IA of the ring component 1 can only be inserted into the thru hole 2E of the housing 2 when the lever arm 6 is in the up position thereby aligning slot 21 vertically and allowing clearance for shaft IA to traverse through thru hole 2E. Once the ring component 1 is inserted into thru hole 2E of housing 2, the notch 21 prevents rotation of the lever arms 6. FIG. 15 demonstrates how rotation of the lever arms can only be initiated when slot 20 of the ring component 1 is aligned with notch 21 allowing rotation of the lever arms and activation of the clamping-cutting device. At the precise location where notch 21 is aligned with slot 20, the ring component 1 is in perfect alignment with the clamping-cutting device 102. It is only when such precise alignment occurs that the operator is able to activate the clamping-cutting device.

Figure 17:
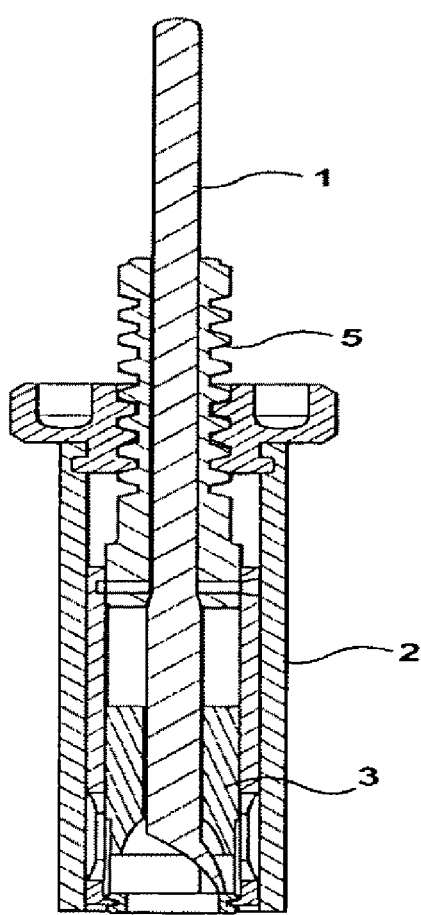
FIG. 17 is a cross section view of yet another alternative embodiment of the present invention.
Figure 18:
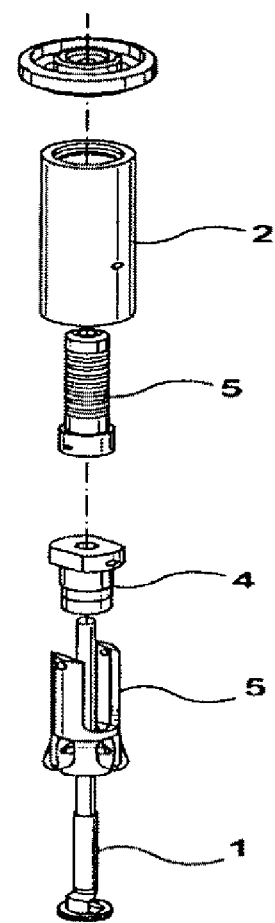
FIG. 18 is an exploded view of the alternative embodiment of FIG. 17.

FIGS. 17 and 18 illustrate other alternative embodiments of the clamping-cutting device of the present invention wherein a clamping-cutting device utilizes a threaded screw to advance the housing over the retractable arms.

FIGS. 19 and 20 illustrate yet other alternative embodiments of the clamping-cutting device of the present invention that uses one lever arm and a lining system.

The following disclosure of the present invention illustrates the self-adjusting pressure applicator adapted for use with a circumcision tool. However, it is contemplated within the scope of the invention for uses on any tissue such as brain or neuron tissue or cardiac vessel, as well as foreskin. Therefore, the invention should not be limited to use with only a circumcision tool as disclosed.

Figures 21A, 21B:
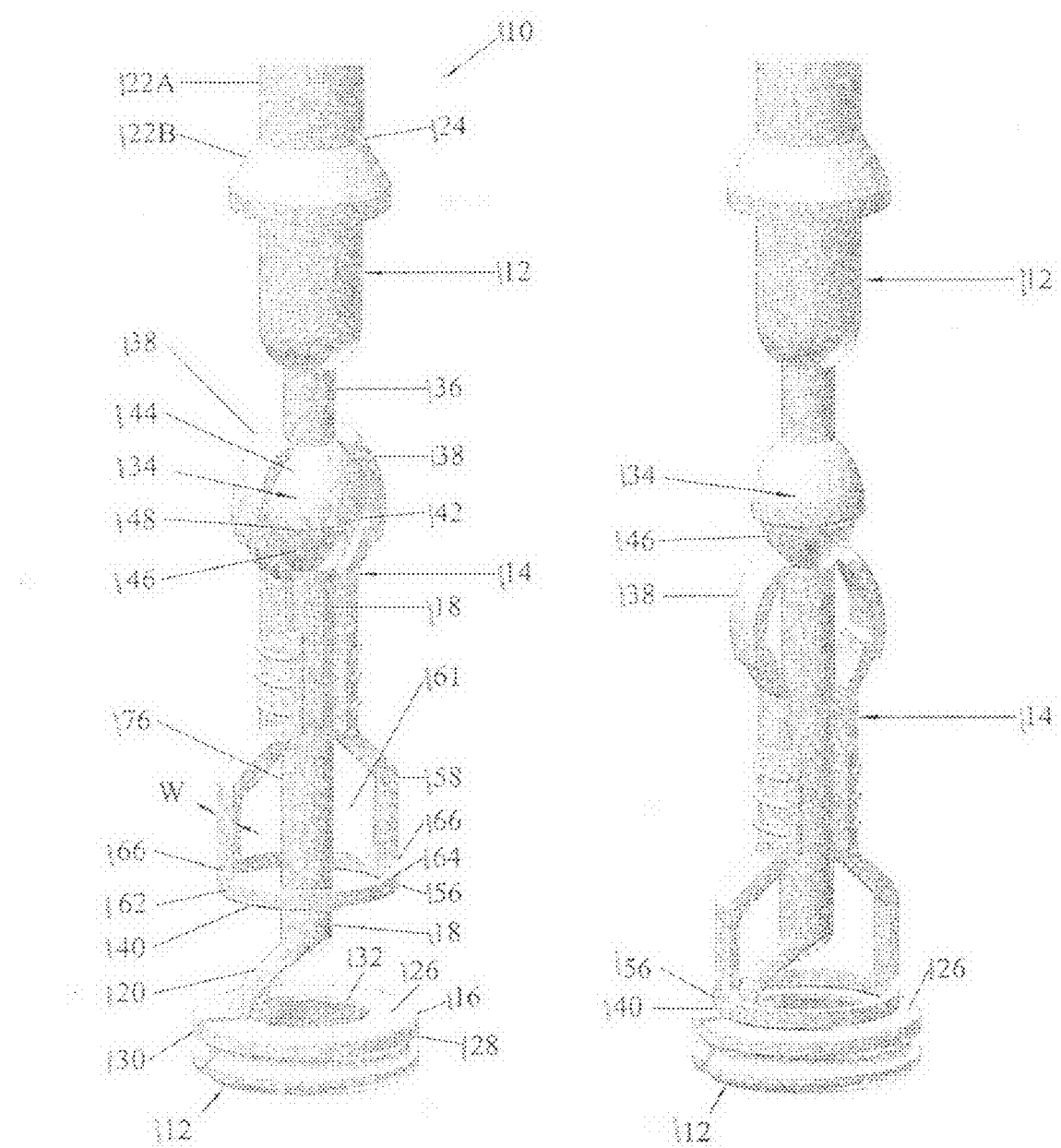
FIG. 21A is a perspective view of one embodiment of the present invention shown in the up position or disengaged.
FIG. 21B is a perspective view of one embodiment of the present invention shown in the down or engaged position.

One embodiment of the self-adjusting pressure applicator 110, illustrated in FIGS. 21A and 21B, includes ring component 112 and foreskin holder 114. FIGS. 21A and 21B illustrate ring component 112 and foreskin holder 114 in the disengaged and engaged positions, respectively. Ring component 112 is a single, one-piece, solid member made from, for example, injection molding of a malleable, elastic material (such as plastic) with an open ring 116 mounted orthogonally to lower shaft 118 by curved member 120, which allows manipulation of ring 116 within the foreskin. Ring component 112 includes a position adjustor 134 that delineates the lower shaft 118 from the upper shaft 136. Ring 116 can include an opening or gap 130 large enough to allow the thickness of the foreskin to enter. Ring 116 can include an inner diameter 132 large enough to receive a predetermined sized glans and shield the glans or head of the penis from being clamped and/or cut. Lower Shaft 118 (not shown) and/or upper shaft 136 (shown) can include a plurality of diameters 122A, 122B to control the insertion of ring component 112 into a clamping-cutting device 200 (disclosed in PCT international application PCT/US2005/022404 and incorporated herein by reference). A shaft diameter change can be delineated by a notch or ledge or, as illustrated in FIG. 21A, shoulder 124 that acts as a stop of ring component 112 into clamping-cutting device 200 (see FIG. 30).

Now turning to FIGS. 31A-D, ring 116 includes a holding/cutting surface 126 on its top surface being adapted to act as a holding surface when foreskin holder 114 is engaged and a cutting surface when cutting edge 202 of blade 204 of clamping-cutting device 200 is pressed down against foreskin 115 interposed between holding/cutting surface 126 and cutting edge 202. Ring 116 may also include grooved outer surface 128 adapted to engage with inward radial extension or projection 206 of retractable arm 208 to hold ring component 112 in a stationary position relative to clamping-cutting device 200 (See FIGS. 31A-B) during the clamping/cutting operation, such that the foreskin 115 is trapped between the grooved outer surface 128 and the radial extension 206 of the retractable arms 208 (See FIGS. 31A-B). Grooved outer surface 128 will interact with inward radial extension 206 to crush the foreskin against grooved outer surface 128 and contemporaneously hold ring component 112 in position while circular blade 204 is delivered to make the incision in the foreskin.

Now returning to FIGS. 21A and 21B, one example of the self-adjusting pressure applicator 110 illustrates position adjustor 134 that cooperates with malleable, spring-like opposing arms 138 of foreskin holder 114 to apply a hands-free self-adjusting constant pressure force upon the foreskin disposed between lower surface 140 of foreskin holder 114 (FIGS. 21A and 21B) and holding/cutting surface 126 of ring component 112. Malleable arms 138 and position adjustor 134 act as pressure force generators. This arrangement provides for flexibility in positioning the foreskin prior to cutting while maintaining a predetermined pressure force. One embodiment for the present invention applies a pressure force between 50 and 200 grams to the tissue when engaged. Another embodiment applies a pressure force of about 181 grams of force to the tissue when engaged. The pressure force is exerted along a common centerline of ring component 112 and foreskin holder 114.

One embodiment of the present invention is engaged only long enough to insert the self-adjusting pressure applicator 110 into the clamp, activate the clamp or otherwise cut the foreskin, thereby removing the retained foreskin from the patient. For example, the self-adjusting pressure applicator 110 can be engaged ranging from about 30 seconds to about one minute, the foreskin can be positioned between the two components, the clamp applied, and the retained foreskin crushed and excised. The agility, flexibility, and simplicity of the self-adjusting pressure applicator 110 allows for repositioning of the foreskin to assure substantially full or entire circumferential retention of the foreskin or tissue. Such minor adjustments can be made with great precision within a short period of time and with no tissue damage. Providing full circumferential retention of the foreskin or tissue along the crushing and cutting surface results in an improvement of the surgical removal of the foreskin or tissue without the use of barbs, pins, clips, or hemostats.

Another embodiment of the self-adjusting pressure applicator 110 applies the pressure force indefinitely to the tissue being retained allowing for prolonged surgical manipulation of that tissue without causing permanent injury.

One embodiment of position adjustor 134 is generally a circular body, having a tapered surface, and can be, for example, in the form of two unequal half spheres (similar to football halves) that create a shoulder or lip 142 when joined together. An upper half sphere 144 can have a diameter at the joining interface 148 larger then the mating diameter of lower half sphere 146. Spheres 144, 146 each have a tapered surface to facilitate the upward and downward movement of malleable arms 138 on the spheres 144, 146. The shoulder 142 formed at interface 148 acts as a malleable arm stop to inhibit the upward progress of malleable arms 138 as the foreskin is pulled upward to position it for crushing and cutting. The malleable arms 138 must be spread open to fit over shoulder 142 and into the disengaged position. The concave configuration of malleable arms 138 can be sized and shaped similar to spheres 144, 146 for containment of the foreskin holder 114 while in the disengaged position (FIG. 21A) and for spring-back properties while in the engaged position (FIG. 21B). The tapered surface of lower sphere 146 can be sized and shaped to provide the desired predetermined pressure force taking into consideration the spring-back force of malleable arms 138. Malleable arms 138 must always be in contact with lower sphere 146 to maintain a constant predetermined pressure on to the foreskin when foreskin is disposed between lower surface 140 of foreskin holder 114 and holding/cutting surface 126 of the ring component 112.

In furtherance of the description to hold foreskin in a precise location, when the foreskin holder 114 is positioned in the down or engaged position, malleable arms 138 of the foreskin holder 114 interact with the lower tapered surface 146 of position adjustor 134 forming a spring-like mechanism to create a force in the direction towards holding/cutting surface 116 and away from position adjustor 134. The spring-like mechanism exerts a force that holds foreskin holder 114 in place along the holding/cutting surface 126 of ring component 112. The pressure force in turn holds the foreskin in place that is positioned between the holding/cutting surface 126 and the foreskin holder ring portion 156. Ring portion 156 at the base of the foreskin holder 114 applies a 360° circumferential force to the holding/cutting surface 126 to achieve a substantially constant circumferential pressure or holding force. Shoulder 142 of the position adjustor 134 along interface 148 acts as a latch allowing for malleable arms 138 to move down lower shaft 118, but prevents inadvertent movement of foreskin holder 114 back up into the disengaged position. Shoulder 142 ensures that malleable arms 138 and lower tapered surface 146 maintain in an axial position that generates the spring-like force holding the foreskin holder 114 in place relative to holding/cutting surface 126 of ring component 112. Ring portion 156 of foreskin holder 114 is preferably supported by two support arms 158 (discussed in detail below) that allow for easy visibility and access to the foreskin that becomes retained within the cavity 161 of foreskin holder 114.

Figure 22:
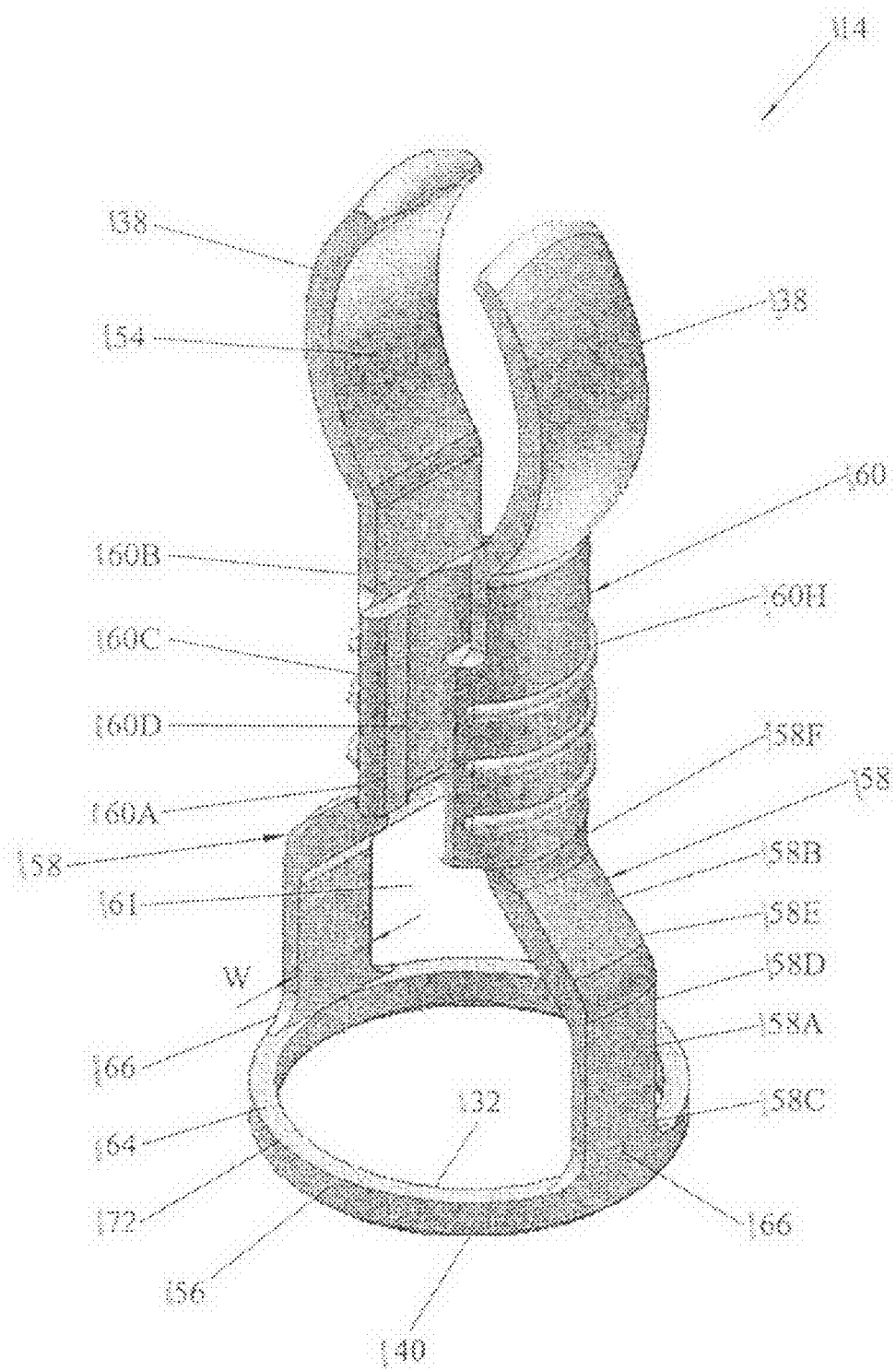
FIG. 22 is a perspective view of an exemplary foreskin holder of the present invention of FIG. 1.

Now turning to FIG. 22 for a complete discussion of foreskin holder 114. One example of the foreskin holder 114 is a single, one-piece, injected molded, solid member constructed of malleable, elastic material (such as plastic). As mentioned above, foreskin holder 114 includes a ring portion 156, a pair of support arms 158, a C-shaped sleeve 160, and a pair of malleable arms 138. Ring portion 156 is configured to align juxtaposition to the holding/cutting surface 126 of ring 116 (see FIG. 21A) of the ring component 112. Ring portion 156 is generally circular with an inner diameter 132, outer diameter 172, a bottom surface 140, and a top surface 164. Bottom surface 140 is a pressure surface that contacts and applies pressure to the foreskin disposed between the holding/cutting surface 126 of the ring component 112.

As discussed above, malleable arms 138 will exert a downward force caused by its interaction with a position adjustor 134 on the modified ring component 112. The spring coefficient of the malleable arms 138 can be derived by well known methods to accommodate the desired pressure force. The desired pressure force can be determined by knowing, among other characteristics, thickness of tissues including but not limited to foreskin, brain or neuron tissue, or cardiac vessel. The downward force is translated through C-shaped sleeve 160 to support arms 158. Supports arms 158 applies the translated force to ring portion 156 at interconnect points 166. The force will be substantially evenly distributed along lower surface 140 when lower surface 140 is in contact with foreskin disposed between lower surface 140 and holding/cutting surface 126 of the ring component 112. The force or contact pressure distribution along to lower surface 140 is a function of width W of support arms 158 and the rigidity of ring portion 156. For example, the wider the support arms 158, the more ring portion surface area in the direct load path of the translated force. Ring portion 156 would bend less when the ring portion 156 is more rigid. Bending of ring portion 156 could cause a reduction of the contact pressure along lower surface 140 as a function of circumferential distance from the interconnect points 166.

Though a pair of independently deflectable malleable arms have been used to illustrate a spring-like mechanism to apply a pressure force, it should be appreciated that there are many suitable combinations of arm (deflectable or rigid) or spring-like mechanisms incorporated into the body of the position adjustor 134 that will achieve the desired results. The invention should not be limited to only the embodiments disclosed in this application.

Now turning in FIGS. 23A-C, one embodiment of a support arm 158 can include one or more sections. Shown as an example is support arm 158 having two sections 158A, 158B. Two support arms 158 provides for easier visibility and access to the foreskin that becomes retained within the foreskin holder 114. Section 158A is attached at one of its ends 158C to either top surface 164 or to the inner diameter 133 (FIG. 23C) or to the outer diameter 172. One embodiment of Section 158A can be oriented orthogonal to ring portion 156. However any angle α (FIG. 23B) that applies evenly distributed forces along lower surface 140 of ring portion 156 is acceptable. Section 158B is attached at a predetermined angle Ø at one of its ends 158E to the other end 158D of section 158A, and at its other end 158F to C-shaped sleeve 160 at its end 160A at a predetermined angle β. The angular relationships between sections 158A and 158B and C-shaped sleeve 160 create an inward taper of support arms 158. The predetermined angles α, Ø, and β, and therefore the support arm taper, can be variable to accommodate the independent optimization of ring portion 156 and C-shaped sleeve 160, and/or to optimize the contact pressure along lower surface 140. In the case where Ø is 180°, there will only be one section 158. Though the preferred number of support arms is two, any number of support arms is acceptable and within the contemplation of the invention.

Continuing with the embodiment illustrated in FIG. 23B, each malleable arm 138 is attached at one of its ends 138A to end 160B of C-shaped sleeve 160 and its other end 138B is free to independently flex or deflect (X) and form a gap (Y) at rest. Free ends 138B can deflect to predetermined distance X under predetermined load or force conditions (discussed in detail below). The flexed or deflected malleable arms act like a spring storing energy to produce a spring back force, which is a function of the deflection distance X. The larger the deflection distance X, the more spring-back force will be created. Since the spring back force is also a function of the materials property, for example the modulus of elasticity, material selection is also important in determining the desired spring back force. It will become apparent later in this application that the spring back force will act upon a position adjustor 134 of ring component 112 to result in a downward movement of foreskin holder 114 that applies the pressure force to the foreskin disposed between lower surface 140 and holding/cutting surface 126 of ring component 112. Malleable arms 138 can be of any configuration that results in the desired spring back force working in conjunction with position adjustor 134 of ring component 112. For example, malleable arms 138 can have a concave surface 154 and be opposingly oriented to each other. As discussed above, the type of materials, dimensions (thickness, width, length) of malleable arms 138, and/or shape of malleable arms 138 (concave or convex) are derivable from the desired pressure force to be applied to a target tissue, such as foreskin, brain or neuro tissue, or cardiac vessel.

Figure 24A:
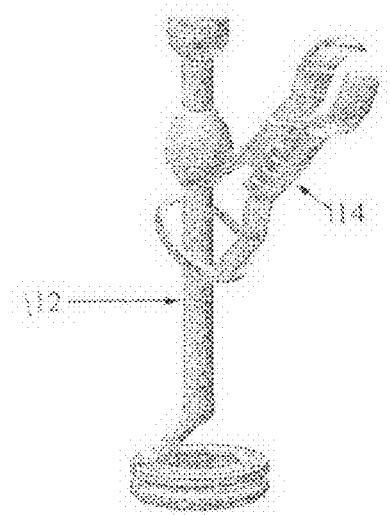
FIGS. 24A-C illustrate the assembly of the foreskin holder of FIG. 22 on to an exemplary embodiment of the ring component.
Figure 24B:
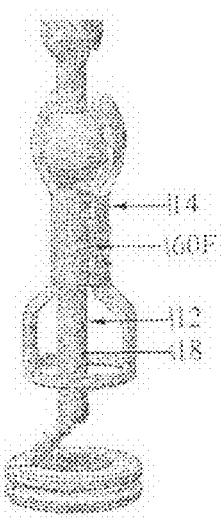
Figure 24C:
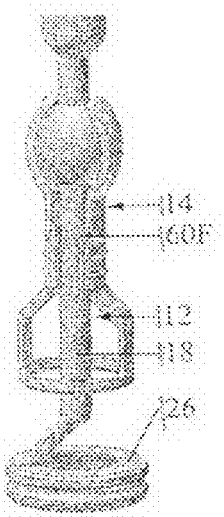
Figure 25:
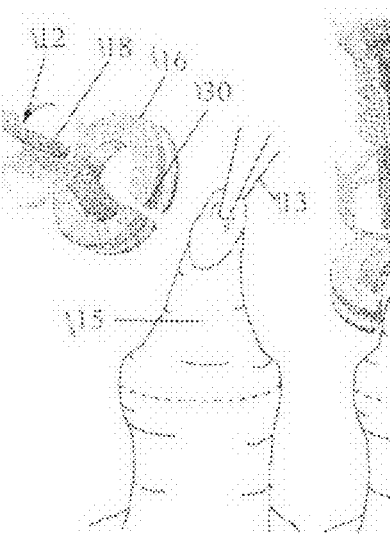
FIGS. 25-28 are pictorial views of the ring component being inserted into the foreskin of a penis.
Figure 26:
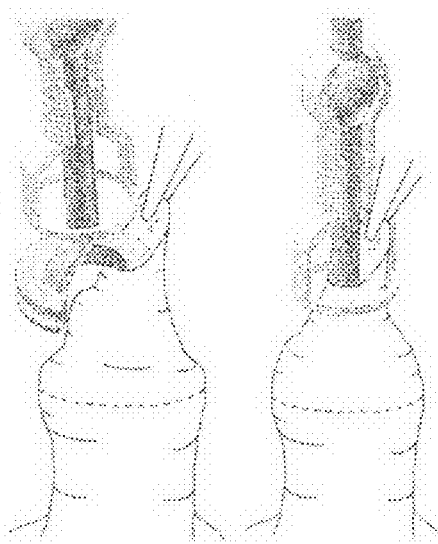
Figure 27:
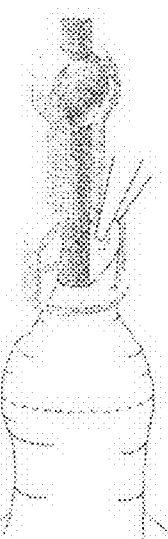
Figure 28:
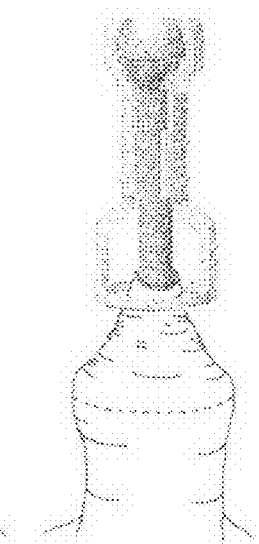

Now turning to FIG. 23C, C-shaped sleeve 160 in generally cylindrical in shape and hollow having an outer diameter 160C, an inner diameter 160D, and two circumferential ends 160E, which form slot 160F with gap 160G. Gap 160G is less than inner diameter 160D of C-shaped sleeve 160 and less than the outer diameter 176 of lower shaft 118 of ring component 112 (FIG. 21A). C-shape sleeve 160 has sufficient elastic properties such that gap 160G will open as lower shaft 118 is inserted through slot 160F and gap 160G will close or return to its original gap distance 160G after insertion of lower shaft 118 into slot 160F. Once lower shaft 118 is inserted through slot 160F, it is trapped or entrained within C-shaped sleeve 160 and only permitted to move along in a longitudinal path within C-shape sleeve 160 because outer diameter 176 is smaller than inner diameter 160D to allow for lower shaft 118 to move longitudinally within inner diameter 160D. Ends 160E can be rounded to facilitate easier insertion of lower shaft 118 through slot 160F. FIGS. 24A-C illustrate foreskin holder 114 (female component) being positioned on ring component 112 (male component) (FIG. 24A), alignment of slot 160F of foreskin holder 114 with lower shaft 118 of ring component 112 prior to insertion (FIG. 24B), and foreskin holder 114 slidably connected with ring component 112 after insertion of lower shaft 118 through slot 160F (FIG. 24C).

One embodiment of outer diameter 160C can include finger grips 160H to facilitate a better grip for raising and lowering foreskin holder 114 relative to ring component 112. Finger grips 160H can be one or more projections. As shown in FIGS. 23A and 23B, three projections 160H are circumferentially oriented parallel to each other along outer diameter 160C. Any cluster or grouping of projections are acceptable as well as any surface treatment that creates a frictional condition between the user's fingers and outer diameter 160C.

FIGS. 25-28 demonstrate an example of the insertion of ring 116 into the foreskin 115. As discussed above, gap 130 allows entry of ring 116 into foreskin 115. Foreskin 115 is held by an atraumatic forceps 113 while gap 130 is positioned to enter foreskin 115. With a pair of non-traumatic forceps, the foreskin is gently grasped and foreskin 115 is guided into the gap 130 of ring 116. With a screw-like motion of lower shaft 118 of ring component 112, the ring 116 is advanced in, down, and around the inner aspect of the foreskin 115. The gap 130 in ring 116 allows the ring 116 to be advanced into the foreskin with a smooth, non traumatic fluid screwing motion. Once ring 116 is fully inserted and resides just beneath foreskin 115, it can be pushed down slowly toward the glans to free any adhesions but to be surrounded by foreskin 115. Inside foreskin 115, gap 130 is closed by the elastic nature of the foreskin 115 attempting to return to its state after being stretched during the insertion of ring 116. The closed ring 116, inside the foreskin of the penis, residing just above the glans or tip of the penis, is then used as the compressive surface for any number of clamps, such as inward radial extension 206 (tongue) and mating recess 207 (groove) (FIG. 31A), and its top surface 126 acts as a combination glans shield, cutting surface for blade 204 as it cuts the foreskin, and foreskin holder when cooperating with foreskin holder 114.

Figure 29A:
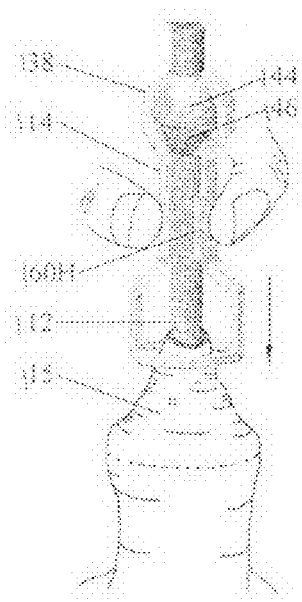
FIGS. 29A-C illustrate the positioning of foreskin between the foreskin holder and the ring component of FIGS. 24A-C.
Figure 29B:
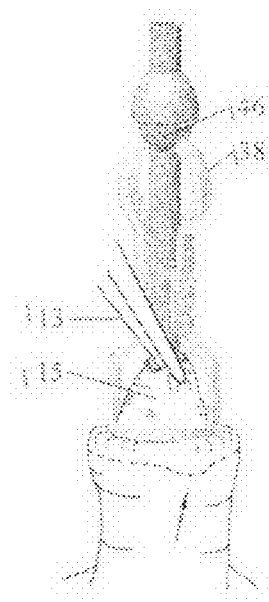
Figure 29C:
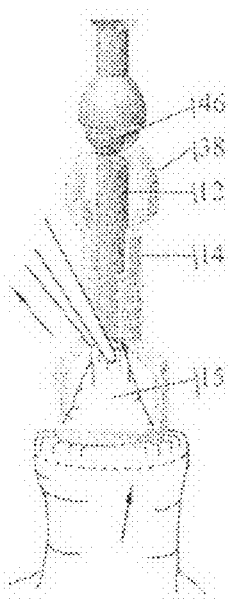

FIGS. 29A-C illustrate the operation of foreskin holder 114 after foreskin is positioned on the ring 116 of ring component 112 (hidden beneath foreskin 115). The operator pinches or grips finger grips 160H of foreskin holder 114 and pushes foreskin holder 114 down towards holding/cutting surface 126 (hidden beneath foreskin 115) (FIG. 29A). The dashed line represents the desired circular foreskin cutting circumference. Malleable arms 138 automatically open as malleable arms 138 move down upper sphere 144 and then automatically close as malleable arms 138 transition to move down lower sphere 146. The operator uses forceps 113 to grab the foreskin 115 for initial positioning for a substantially circular cut, shown as a dashed line (FIG. 29B). After initial positioning, the operator pulls the foreskin 115 substantially upwards (FIG. 29C). Foreskin holder 114 may advance upward on to lower sphere 146. As foreskin holder 114 advances upward the spring back force of malleable arms 138 increases and the downward pressure increases to counter the upward pull on the foreskin and to maintain a substantially constant circumferential pressure force onto the foreskin. Repositioning of the forceps may be necessary to assure the foreskin is evenly distributed around holding/cutting surface 126 of ring component 112 (hidden beneath foreskin 115) for a substantially circular cut (dashed line).

Figure 30:
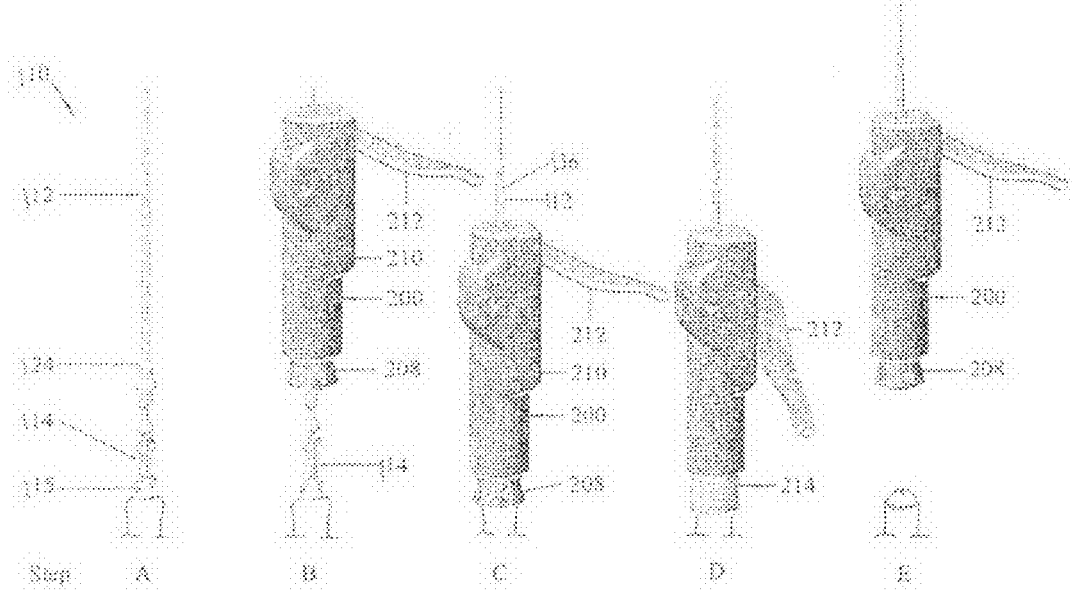
FIG. 30 are pictorial views illustrating use of the open ring of the present invention with a clamping-cutting device.

FIG. 30 illustrates one embodiment of the self-adjusting pressure applicator 110 adapted for use with a circumcision clamping-cutting device 200 (disclosed in PCT international application PCT/US2005/022404 and incorporated herein by reference) adapted to cooperate with each other. Step A: Ring 116 (hidden beneath foreskin) of ring component 112 is inserted into the foreskin 115 of the penis, as discussed above. Step B: Clamping-cutting device 200 is set in the open position with lever arm 212 rotated up and retractable arms 208 extending fully through the bottom of housing 210 and sleeve 214. Step C: Clamping-cutting device 200 is inserted onto upper shaft 136 of ring component 112. Downward movement of clamping-cutting device 200 and housing 210 onto upper shaft 136 is stopped when shoulder 124 contacts bottom face of an internal thru hole (not shown). Step D: Lever arm 212 is activated downward to advance sleeve 214 downward over retractable arms 208 causing the clamping force and delivering the internal circular blade 204 (FIG. 31A) to the foreskin 115. Sleeve 214 moves downwardly over retractable arms 208 causing retractable arms 208 to radially close on to and to exert lateral compressive force against the foreskin 115. Turning to FIGS. 30 and 31A and B, retractable arms 208 exert sufficient lateral compressive force or clamping such that inward radial extensions 206 (FIG. 31A) of retractable arms 208 forces the foreskin 115 into grooved outer surface 128 of ring 116, thereby clamping the foreskin 115. As sleeve 214 is advanced even further over the ring 116, blade 204 is delivered to the top surface 164 of ring 116 and creates the circular incision into the foreskin 115 when ring 116 is positioned within clamping-cutting device 200 (FIG. 31B). Using the top surface 164 of ring 116 as the cutting surface that is held in place by the closed retractable arms 208, blade 204 makes a single, clean, circumferential incision on top surface 164 of ring 116, removing the excess foreskin 115. The clamp is left in place for a period of time ensuring adequate crushing and hemostasis. Step E (FIG. 30): Lever arm 212 is lifted upward and retractable arms 208 release ring component 112, lifting sleeve 214 of the clamping-cutting device 200 and lifting blade 204 back up into housing 210 and releasing ring 116. Ring component 112 with severed foreskin is permanently locked within housing (not shown) 210 to prevent inadvertent reuse of any of the components of the device. All components and byproducts of the operation are thrown away, thereby completing the circumcision.

FIGS. 31C and 31D show a bottom view of the clamping arms 208 with radial extensions 206 and corresponding recesses 207 in the open, neutral, pre-clamping position and the closed, clamping position, where radial extensions 206 are substantially retained in recesses 207, respectively.

Figure 32A:
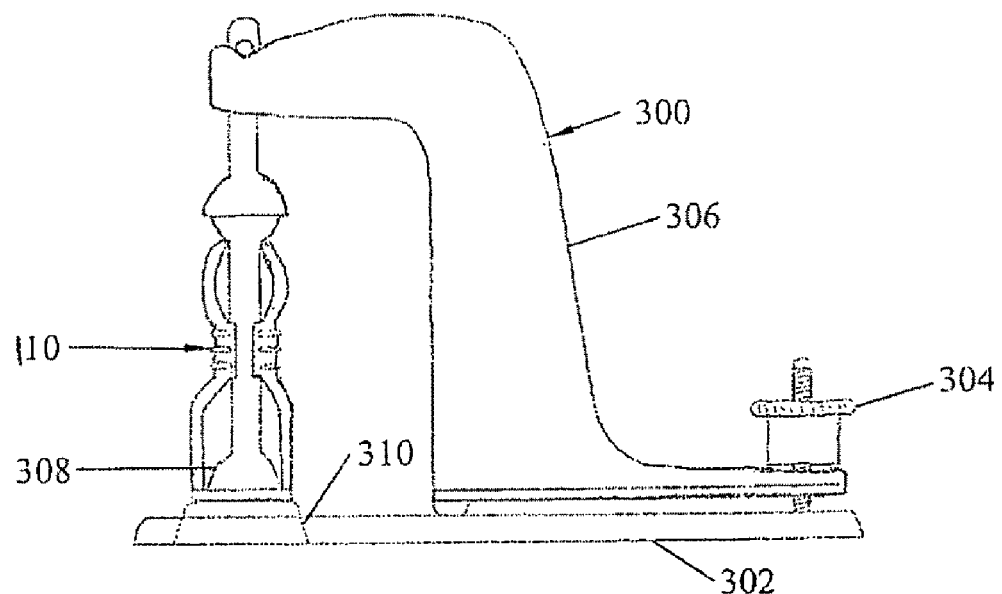
FIGS. 32A is an illustration of the present invention of FIG. 21 adapted for use with a conventional circumcision clamp.

FIG. 32A illustrates the self-adjusting pressure applicator 110 and a conventional type clamp 300, which includes plate 302, nut 304, yolk 306, and bell/stud 308, adapted to cooperate with each other.

Figure 32B:
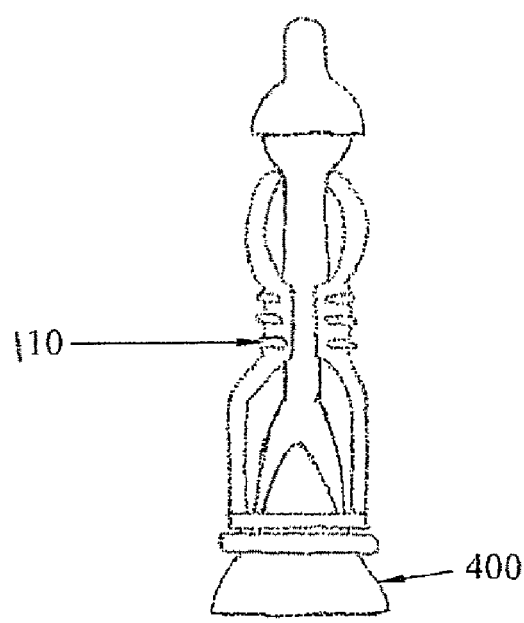
FIG. 32B is an illustration of the present invention of FIG. 21 adapted for use with a conventional circumcision bell.

FIG. 32B illustrates the self-adjusting pressure applicator 110 and a conventional type bell 400 adapted to cooperate with each other.

Figures 33A, 33B:
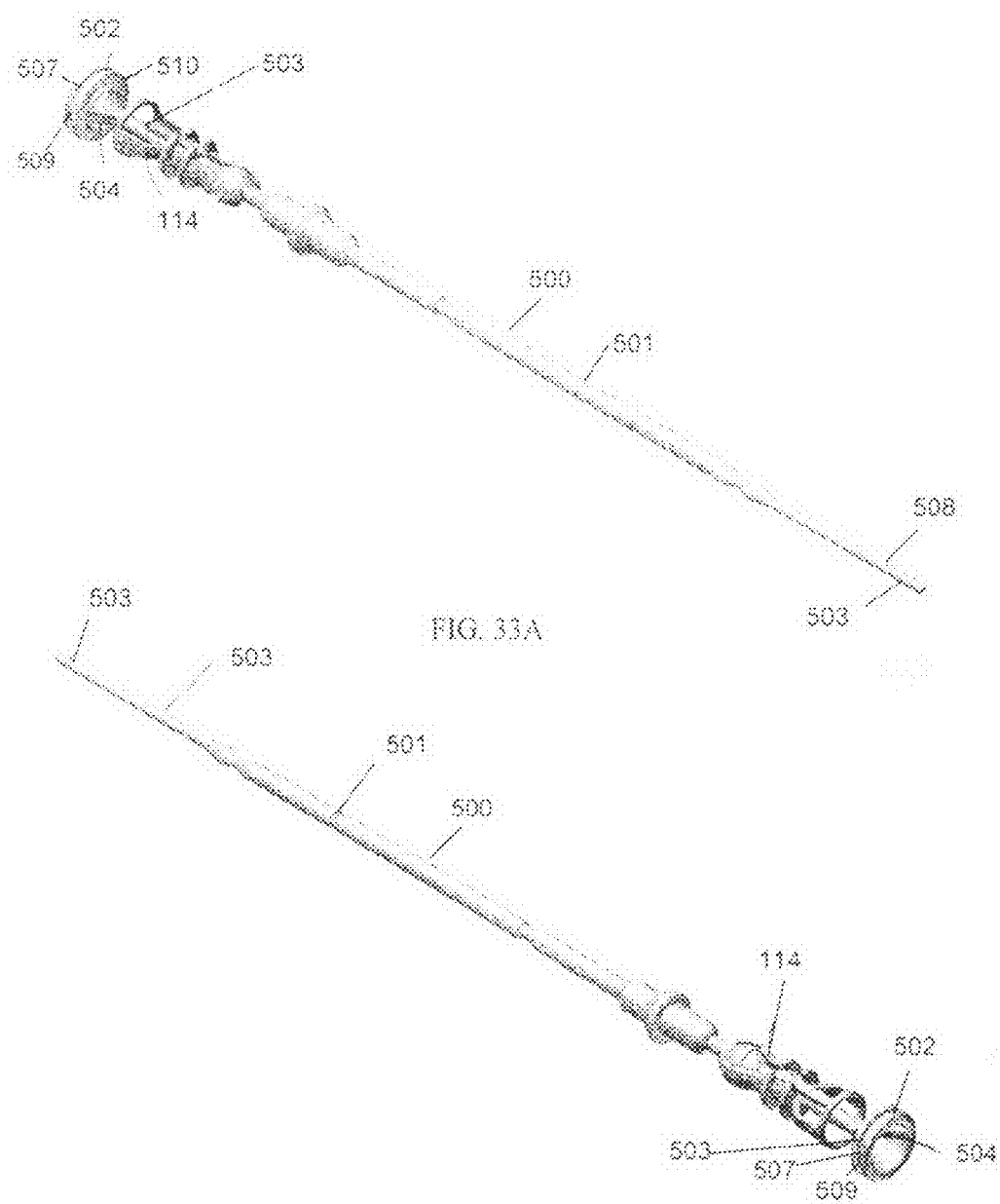
FIGS. 33A-B are pictorial views of a closed ring embodiment.
Figure 34:
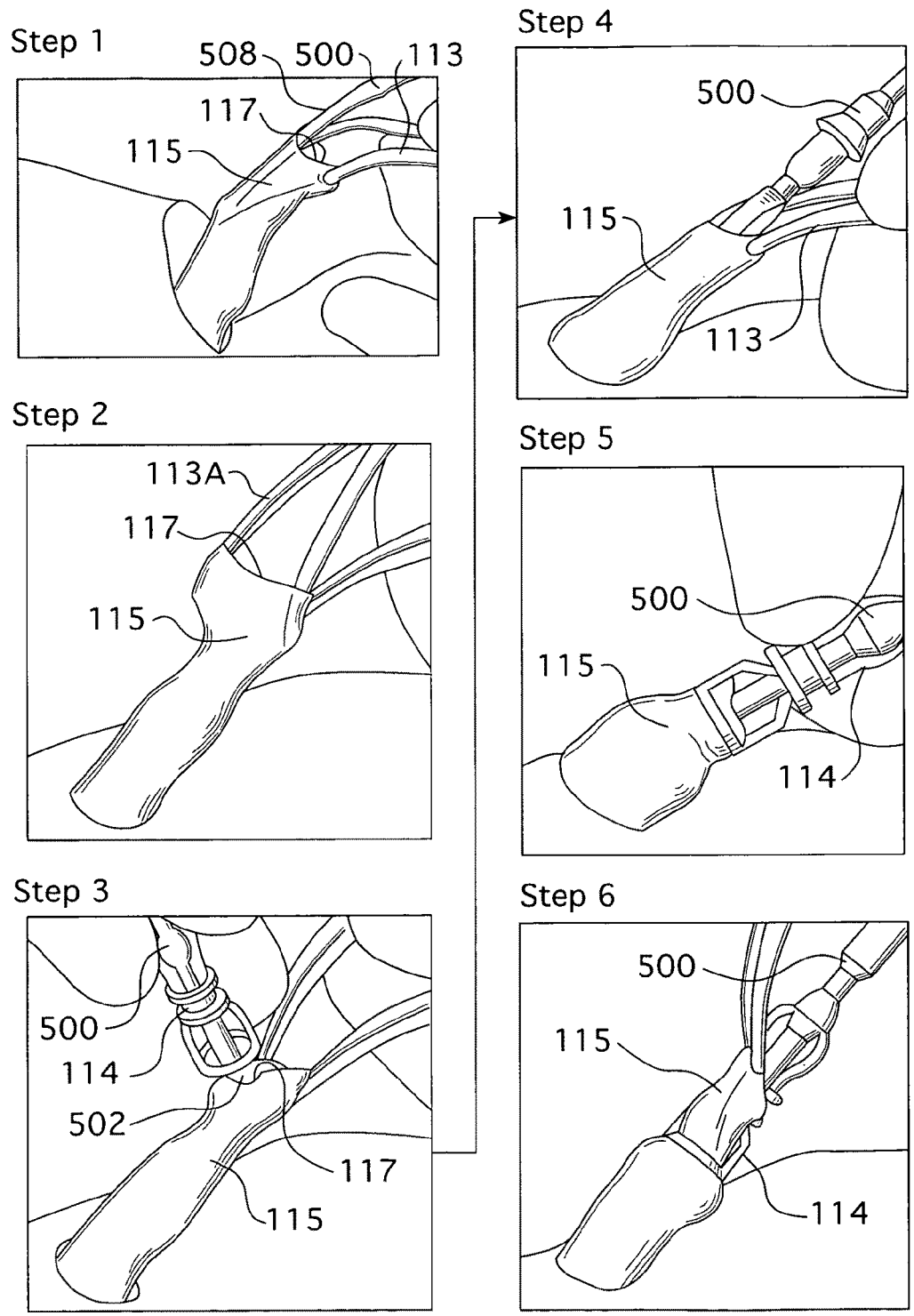
FIG. 34 are pictorial views illustrating use of the closed ring of the present invention with a clamping-cutting device.

Anther embodiment of the present invention includes a ring component 500 having a shaft 501 with a ring 502 (closed ring shown in FIGS. 33A-B or open ring shown in FIG. 5) at a proximal end 503 and a tip 505 at a distal end 508, wherein the ring 502 comprises a radially oriented clamping surface 507 with a circumferential groove 509 and an axially-oriented cutting surface 510. The ring 502 includes a low profile sufficiently sized to fit within a stretched foreskin (discussed in detail below) and the location of the single support 504. These features allow for easier insertion without making a dorsal slit. FIG. 34 demonstrates an example of the insertion of ring 502 into the foreskin 115.

Step 1: Foreskin 115 is held by an atraumatic forceps 113 while the distal end 508 of ring component 500 is positioned through an opening 117 in the foreskin 115 to clear the adhesions separating foreskin 115 from the glans (not shown).

Step 2: A second pair of non-traumatic forceps 113A is inserted into the opening 117 of the foreskin 115 and the foreskin 115 is gently stretched to open the opening 117.

Step 3: Ring 502 (step 3) is inserted into the opening 117.

Step 4: The foreskin 115 is gently grasped by the atraumatic forceps 113 and the ring 502 is advanced in, down, and around the inner aspect of the foreskin 115. Once the ring 502 is fully inserted and resides just beneath foreskin 115, it can be pushed down slowly toward the glans to free any remaining adhesions. The ring 502, inside the foreskin of the penis, residing just above the glans or tip of the penis, is then used as the compressive surface for any number of clamps, such as inward radial extension 206 including a tongue 206A and mating recess or groove 207 (FIG. 31C), and its axially-oriented cutting surface 510 (FIG. 33A) acts as a combination glans shield, cutting surface for blade 204 as it cuts the foreskin 115.

Step 5: When foreskin holder 114 is used, then foreskin holder 114 is advanced downward toward the glans and axially-oriented cutting surface 510.

Step 6: Once foreskin holder 114 is in place securing foreskin 115 disposed between lower surface 140 of foreskin holder 114 (FIGS. 21A and 21B) and axially-oriented cutting surface 510 of ring 502, excess foreskin 115 is pulled upward to assure the cut is clean and symmetrical.

As discussed above, each inward radial extension or projection 206 of the plurality of longitudinal clamping arms 208 comprise a tongue 206A and a groove 207 such that the tongue 206A of the inward radial extension or projection 206 is received within the groove 207 of an adjacent inward radial projection 206 to form a circumferentially overlapping configuration therewith and no radial-through gap therebetween when the plurality of longitudinal clamping arms 208 are in a pre-clamp position to prevent foreskin migrating between the inward radial extension or projections 206 during a clamping operation and pinching the foreskin.

Figure 35A:
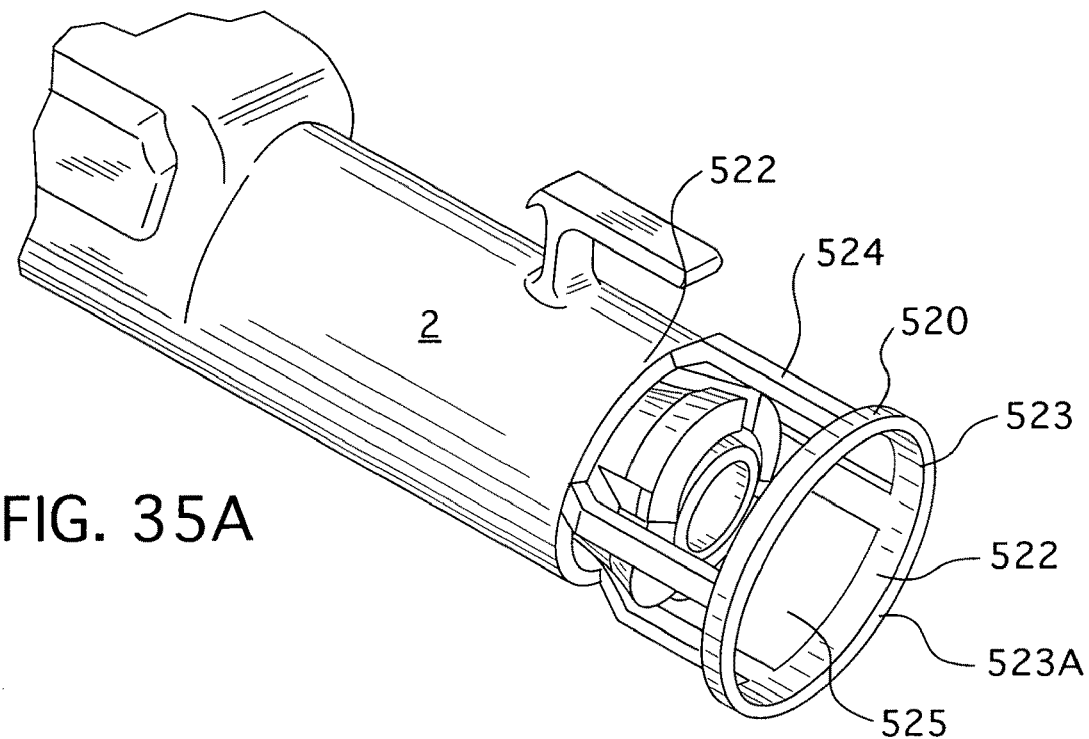
FIGS. 35A-B are pictorial views of the housing of the present invention of one embodiment of a housing extension.
Figure 35B:
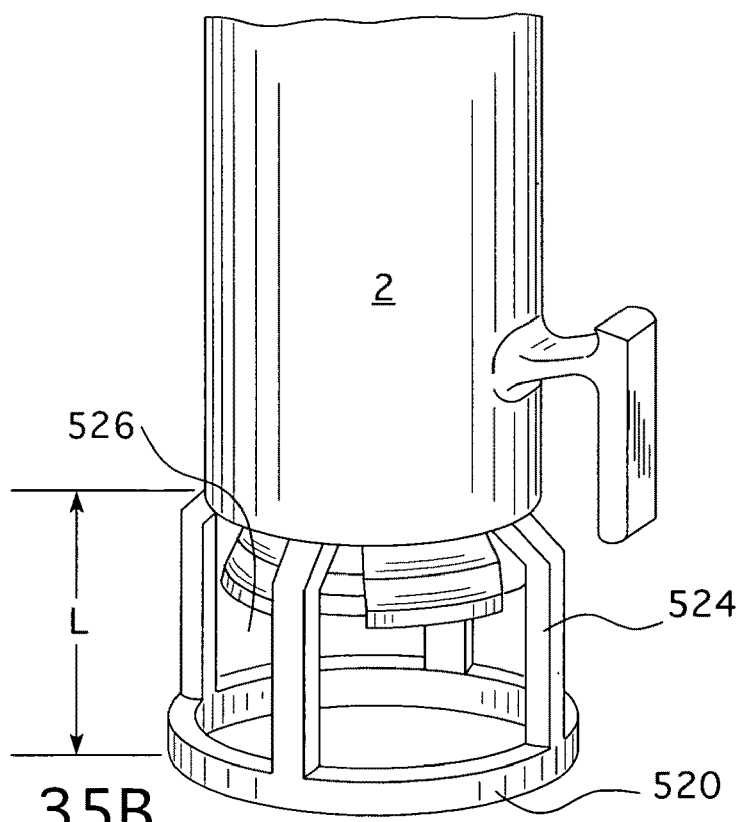

FIGS. 35A-B illustrate an extension 520 at one end 523 of housing 2 to protect the surrounding tissue, such as scrotum, when housing 2 is advanced toward the penis during the crushing and cutting action. Extension 520 can include a base 522 attached to housing 2 with one or more longitudinal supports 524. Base 520 can be circular (as shown) or any suitable geometry, such as semi-circular (not shown), to will prevent surrounding tissue from being damaged during crushing and cutting action. Outer surface 523A contacts body tissue around the penis to cause the stretching of the penis as the clamp mechanism is actuated and the penis is drawn and guided through a bore 525 of the extension 520 toward the housing 2 to ensure the penis is extended a predetermined distance. The length L of the longitudinal supports 524 can be approximately the length of the penis, such as 1 cm. Base 520 can be a continuous surface (as shown) or can be discontinuous with intermittently spaced pads (not shown) having sufficient length and width such that the patient is not pierced or put in significant discomfort. The longitudinal supports 524 and base 520 form spaces 526 providing a viewing area for the user to observe the activity into bore 525.

Figure 36:
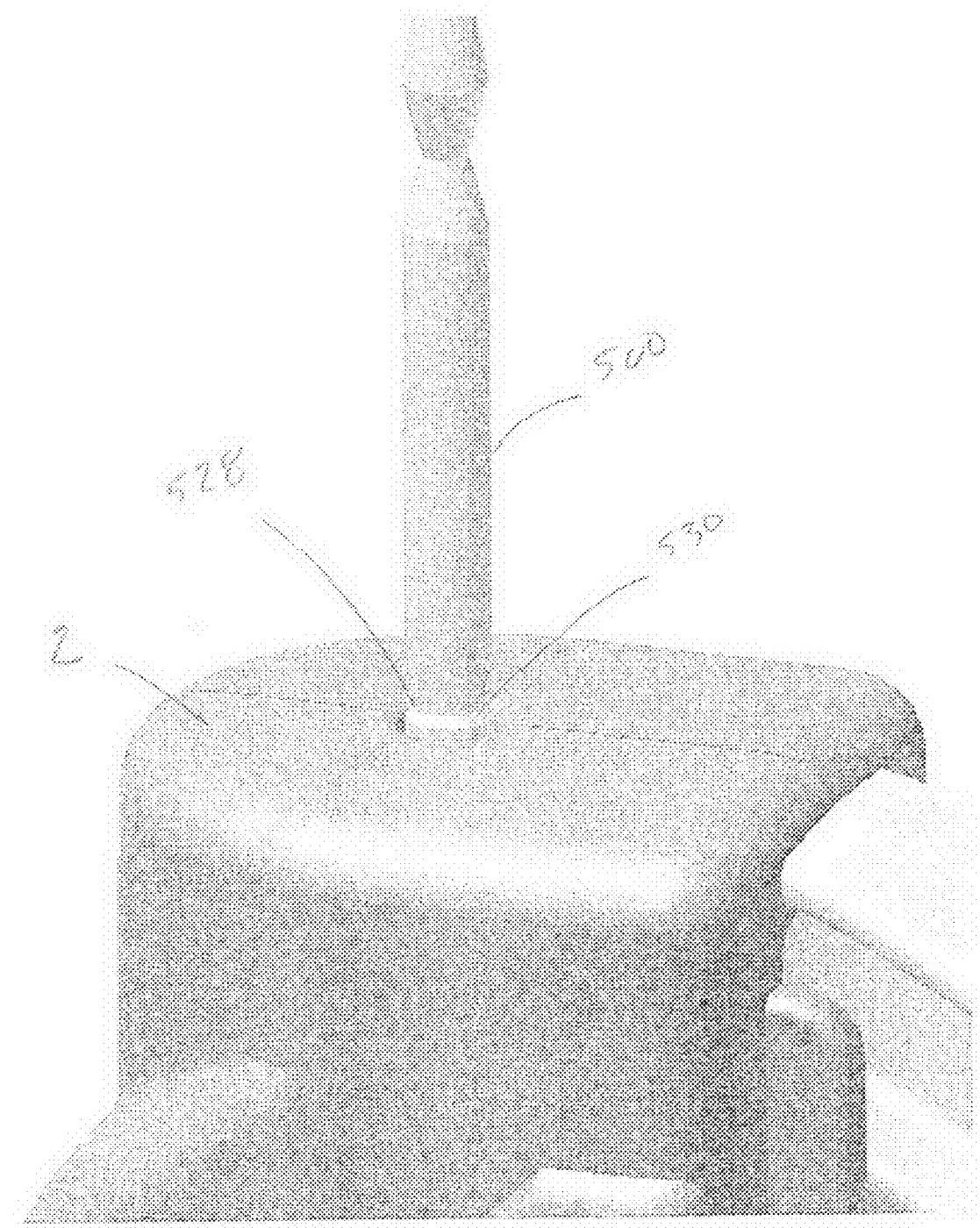
FIG. 36 is a pictorial of one embodiment of a visual indicator on the ring to indicate when the ring is fully engaged in the housing of the present invention.

FIG. 36 illustrates one embodiment of a visual indicator 528 that provides the user with an indication that ring component 500 is in position for actuation of the lever arm 212 (FIG. 30). Visual indication 528 can be a notch 530 with or without a color marking for ease of detection.

Figures 37A, 37B:
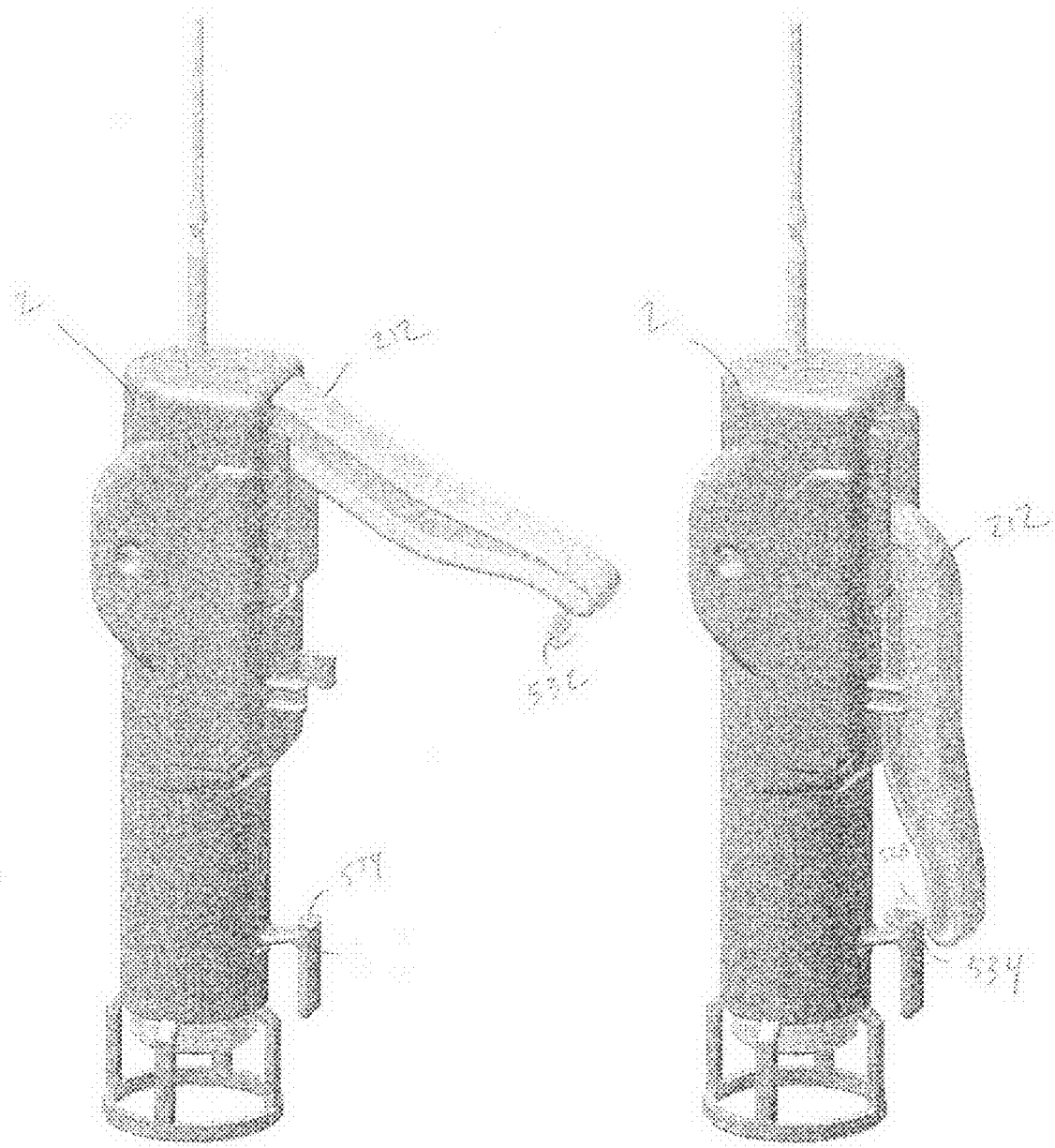
FIGS. 37A-B are pictorial views of one embodiment of the invention disengaged and locked in the engaged position.
Figure 38A:
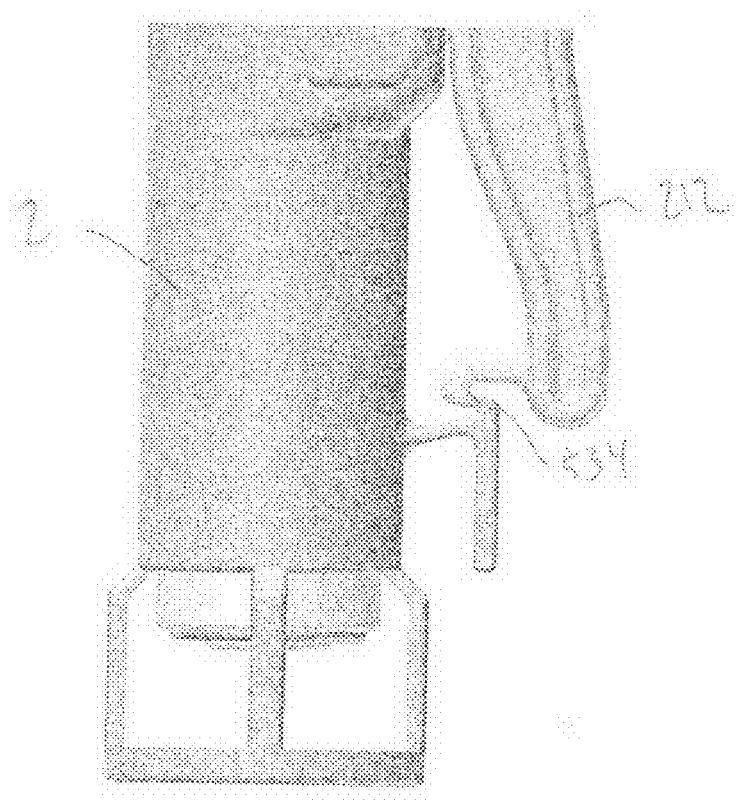
FIG. 38A is a pictorial view of one embodiment of the lever arm locking mechanism engaged illustrating a locked position.
Figure 38B:
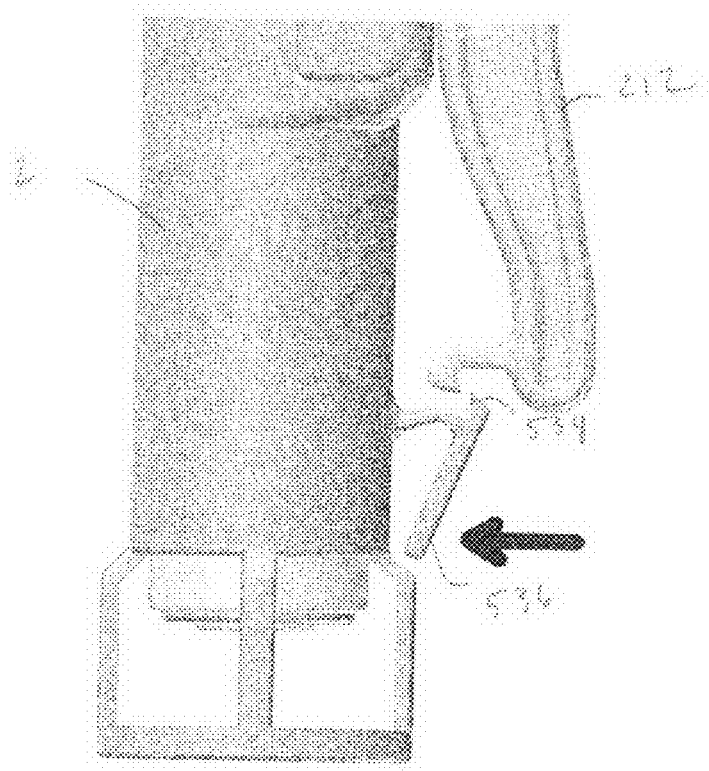
FIG. 38B is a pictorial view of one embodiment of the lever arm locking mechanism illustrating the depression of a tab disengaging the lever arm from a locked position.

FIGS. 37A-B illustrate lever arm 212 prior to actuation and after full actuation, respectively. Lever arm 212 can include a hook 532 having a configuration that interfaces with latch 532 attached to housing 2 to retain lever arm 212 in an engage position to assure adequate crushing and hemostasis. Due to the resistance force of the clamp arms 208 and blade 204, lever arm 212 will rotationally spring back from a maximum actuation position to a position beyond latch 534 towards the disengage position. Latch 532 will mate with hook 532 to retain lever arm 212 in a predetermined position for period determined by the user.

FIGS. 39A-G illustrate an integral radial clamping and an axial cutting device 499 comprising a two-piece housing 2, a core section 537, a lever arm 560, a pair of safety latch mechanisms 535A, 535B, and an actuation mechanism 521. The two-piece housing 2 forming a bore 539 having an open end 511 at a proximal end 541 and a closed end 513 having a hole 515 at a distal end 517 when the two-piece housing is assembled, wherein the hole 515 includes a diameter 519 larger than a diameter Di of the tip 508 of the shaft 501. Core section 537 is encased within the bore 539 of the two-piece housing 2. Core section 537 having an axially oriented blade 544 disposed at a proximal end 541 and a lever arm pivot point 543 at a distal end 545. Lever arm 560, which includes an engagement tooth 556, is pivotally attached to the lever arm pivot point 543 of the core section 537. A pair of safety latch mechanisms 353A, 535B are pivotally attached to the core section 537, wherein the pair of safety latch mechanisms 353A, 535B form an initial gap 527 between inward oriented tabs 560A, 560B prior to actuation of the device. The actuation mechanism 521 is disposed within the bore 539 of the two-piece housing 2 (discussed in detail below).

The actuation mechanism 521 includes a plurality of longitudinal retractable clamping or finger arms 542 at a proximal end 541 of the actuation mechanism 521 having inward radial projections or extensions 529, wherein at least a portion 531 of the plurality of longitudinal retractable clamping or finger arms 542 are disposed outside the bore 539 of the housing 2 forming a gap 533 between the inward radial projections that is greater than a diameter 585 of the circumferential groove 509 of the radially oriented clamping surface 507 of the ring component 550. Though four arms 542 are illustrated in this patent application, the invention is not to be limited to any particular number of arms 542. Actuation mechanism 521 further includes a lever arm engagement gear tooth 558 at a distal end 587 of the actuation mechanism 521 to engage the engagement tooth 556 of the lever arm 560 when the lever arm 560 is actuated with the proper ring component 550 inserted therein.

Once the ring 502 is inserted into the foreskin 115, as shown in FIG. 34 and discussed above, then radial clamping and axial cutting can be performed following the below steps:

Step 1: Inserting and advancing an end 508 of the ring component 550 into an open end 511 of the integral radial clamping and an axial cutting device 499 until a visual or an audible indicator signals to stop advancing. A lock mechanism restraining relative movement of the radial clamping device and the axial cutting device is automatically released while the ring component is advanced into the integral radial clamping and the axial cutting device 499.

Step 2: Actuating the integral radial clamping and the axial cutting device 499.

Step 3A: Decouple the radial clamping device from the axial cutting device when a mis-matched ring component is inserted into the integral radial clamping device and the axial cutting device.

Step 3B: Radially clamping the foreskin against a circumference of the ring and contemporaneously axially cutting the foreskin against the ring with a single actuation motion by the lever arm 560 when a matched ring component is inserted into the integral radial clamping device and the axial cutting device.

Step 4: De-clamping the foreskin after the step of axially cutting.

FIGS. 39A-G further illustrate embodiments of the present invention that include a slip gear 556 and safety latch mechanism 535A, 535B that ensure the present invention can only be used with the correctly sized ring component 550 and only when ring component 550 is correctly inserted into housing 2 and locked in place. Safety latch mechanism 535A, 535B are pivotally mounted to core section 537.

One embodiment of the present invention to prevent use of the wrong the ring component 550 includes complementary limiting features on ring component 550 and in core section 537. Ring component 550 comprises a first limiting section 569 of the shaft 553 having a first diameter 567 and a first section length 589, and a second limiting section 579 of the shaft 553 with a second diameter 591 greater than the first diameter 567 and a second section length 583. The core section 537 comprises a ring component limiting section 547 having a first section 549 with a bore diameter 555 greater than a first diameter 567 of the first limiting section 569 of the shaft 553 to receive the shaft 553 of the ring component 550 there-through and a first section depth 571 (FIG. 39B), and a second section 573 with a bore diameter 575 greater than the second diameter 577 of the second limiting section 579 of the shaft 553 and a second section depth 581, wherein the second section depth 581 of the second limiting section 579 of the core section 537 is substantially equal to the second section length 583 of the second limiting section 579 of the ring component 550. The core section limiting sections 547 and ring component shaft limiting sections 569, 579 may include tapers 579T, 598T.

Figure 41:
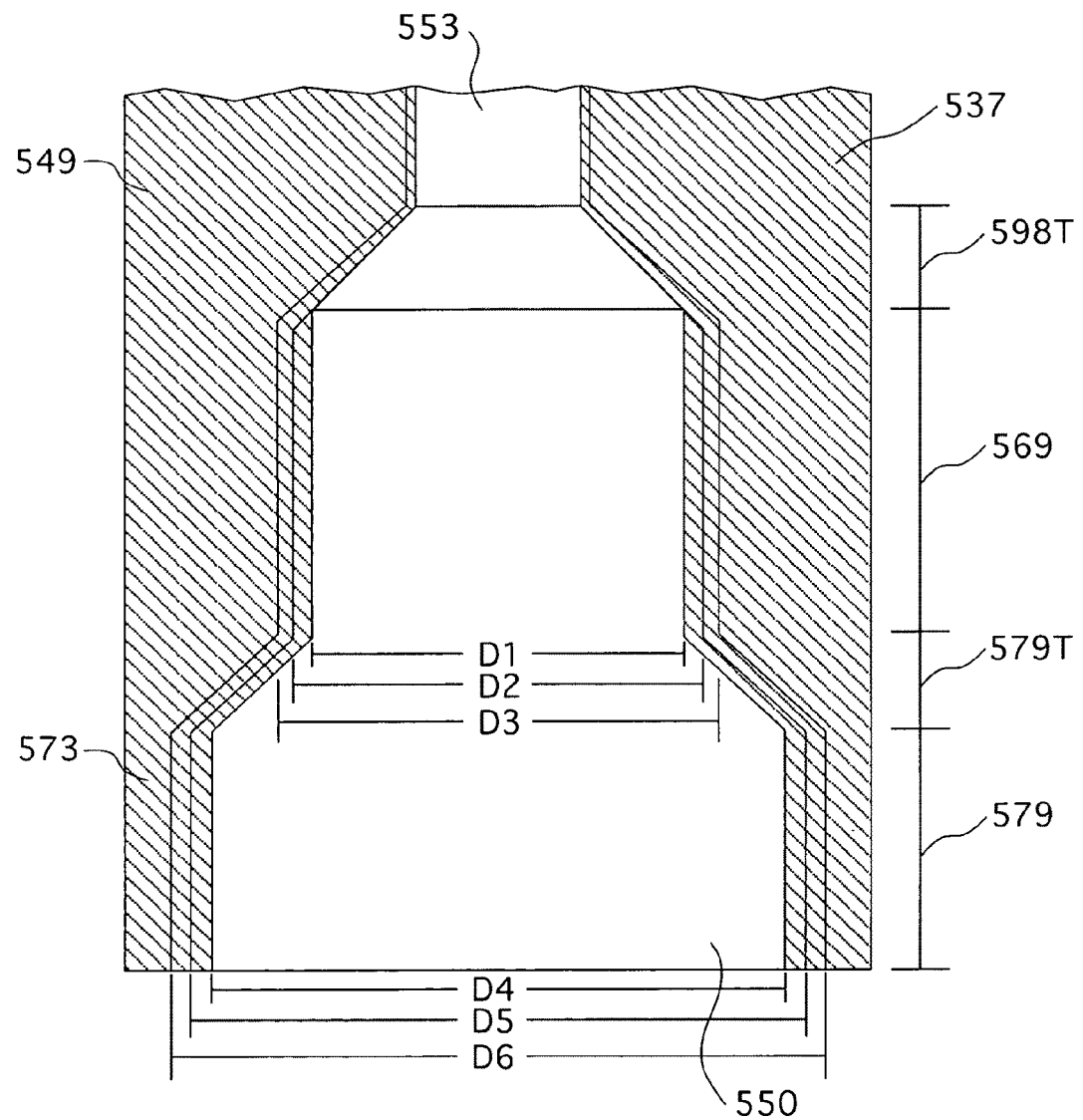
FIGS. 41 and 42A-C illustrate examples of varying diameters of the limiting section of the clamp and varying diameter of the limiting section of the ring component.

FIG. 41 illustrates examples of three embodiments of the diameters D1, D2, D3 of the first limiting section 569 of the shaft 553 and core section first section 549 and the diameters D3, D4, D5 of the second limiting section 579 of the shaft 553 and core section second section 573. The diameters D1, D2, D3 can be matched with any of the diameters D3, D4, D5 to make up to nine combinations of matched shafts 553 and core sections 537.

Figure 42A:
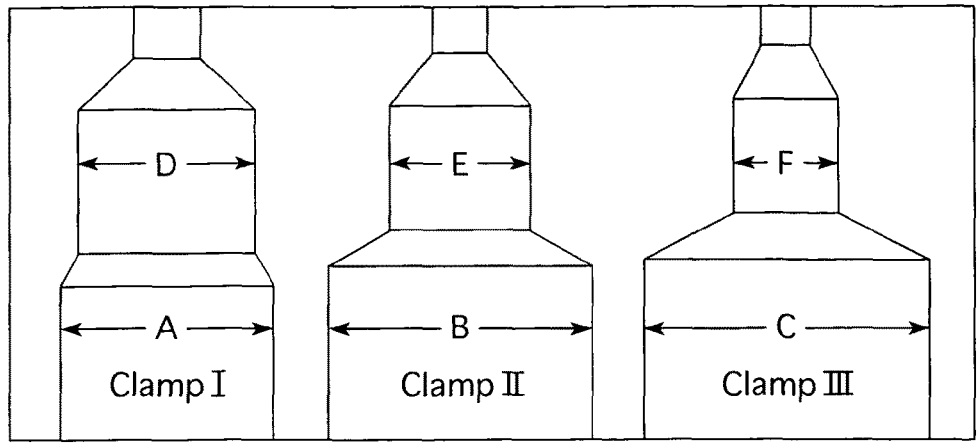
Figure 42B:
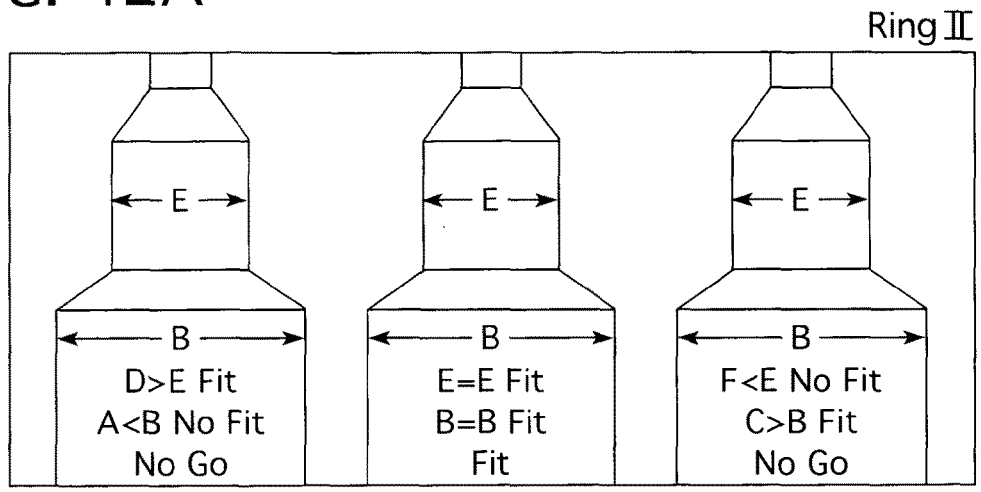
Figure 42C:
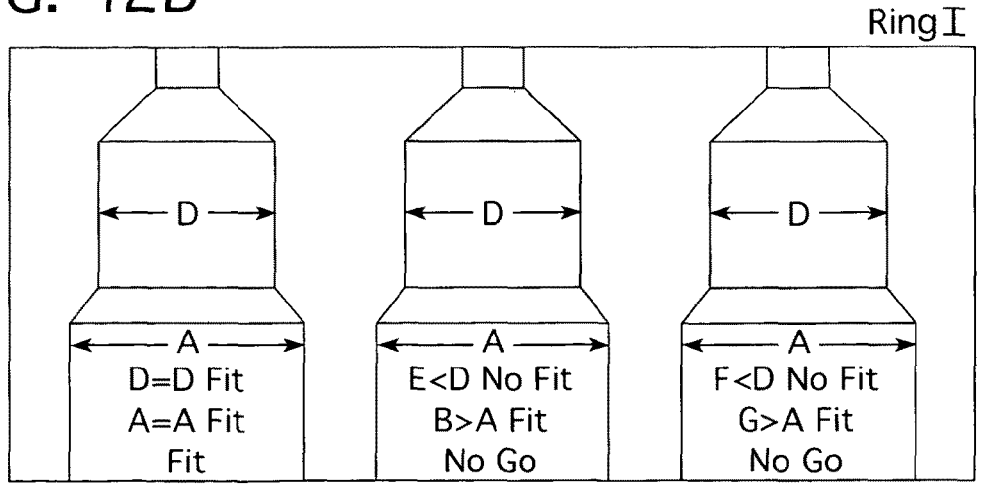

FIGS. 42A-C illustrate a set of three clamps with different core sections and two rings with different limiting sections. FIG. 42A illustrates Clamp I with a core section first section diameter of D and core section second section A, Clamp II with a core section first section diameter of E and core section second section B, and Clamp III with a core section first section diameter of F and core section second section C. FIG. 42C illustrates Ring I having a first limiting section diameter of D and a second limiting section diameter of A. FIG. 42B illustrates Ring II having a first limiting section diameter of E and a second limiting section diameter of B.

With regards to Clamp I and Ring I, first limiting section diameter D of Ring I is equal to core section first section diameter D and second limiting section diameter A of Ring I is equal to core section second section diameter A, so clamp I is a match with Ring I.

With regards to Clamp II and Ring I, first limiting section diameter D of Ring I is greater than core section first section diameter E, so clamp II is not a match with Ring I notwithstanding second limiting section diameter A of Ring I is a fit with core section second section diameter B of Clamp II since diameter A is less than diameter B.

With regards to Clamp III and Ring I, first limiting section diameter D of Ring I is greater than core section first section diameter F, so clamp III is not a match with Ring I notwithstanding second limiting section diameter A of Ring I is a fit with core section second section diameter C of Clamp III since diameter A is less than diameter C.

With regards to Clamp I and Ring II, second limiting section diameter B of Ring II is greater than core section second section diameter A, so clamp I is not a match with Ring II notwithstanding first limiting section diameter E of Ring II is a fit with core section first section diameter D of Clamp I since diameter A is less than diameter B.

With regards to Clamp II and Ring II, first limiting section diameter E of Ring II is equal to core section first section diameter E and second limiting section diameter B of Ring II is equal to core section second section diameter B, so clamp II is a match with Ring II.

With regards to Clamp III and Ring II, first limiting section diameter E of Ring II is greater than core section first section diameter F, so clamp III is not a match with Ring II notwithstanding second limiting section diameter B of Ring II is a fit with core section second section diameter C of Clamp III since diameter B is less than diameter C.

Figure 39A:
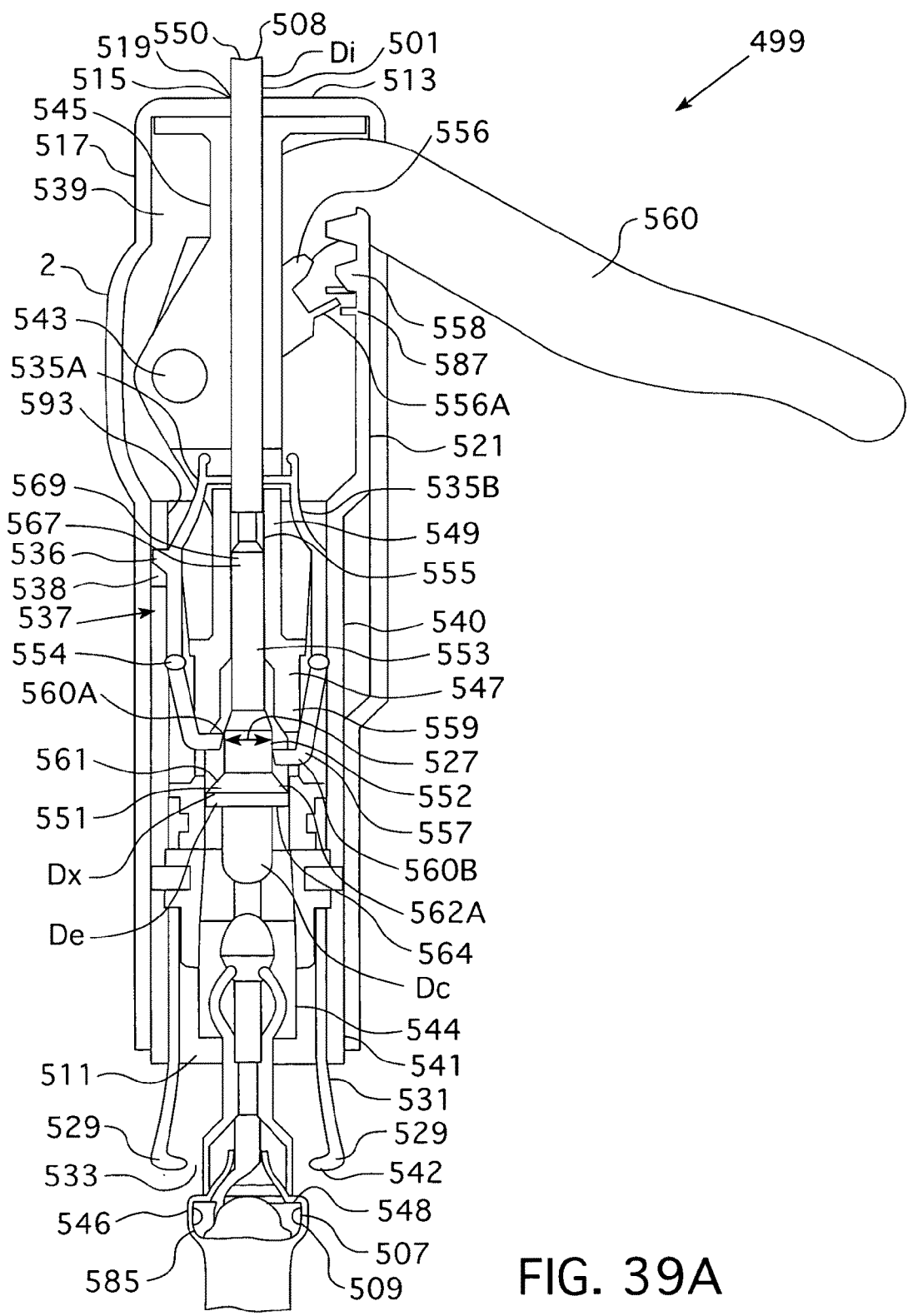
FIGS. 39A-E are sectional views of one embodiment of the present invention illustrating embodiments of a slip gear and safety mechanism to provide for proper advancement of the clamp slide tube and blade.
Figure 39B:
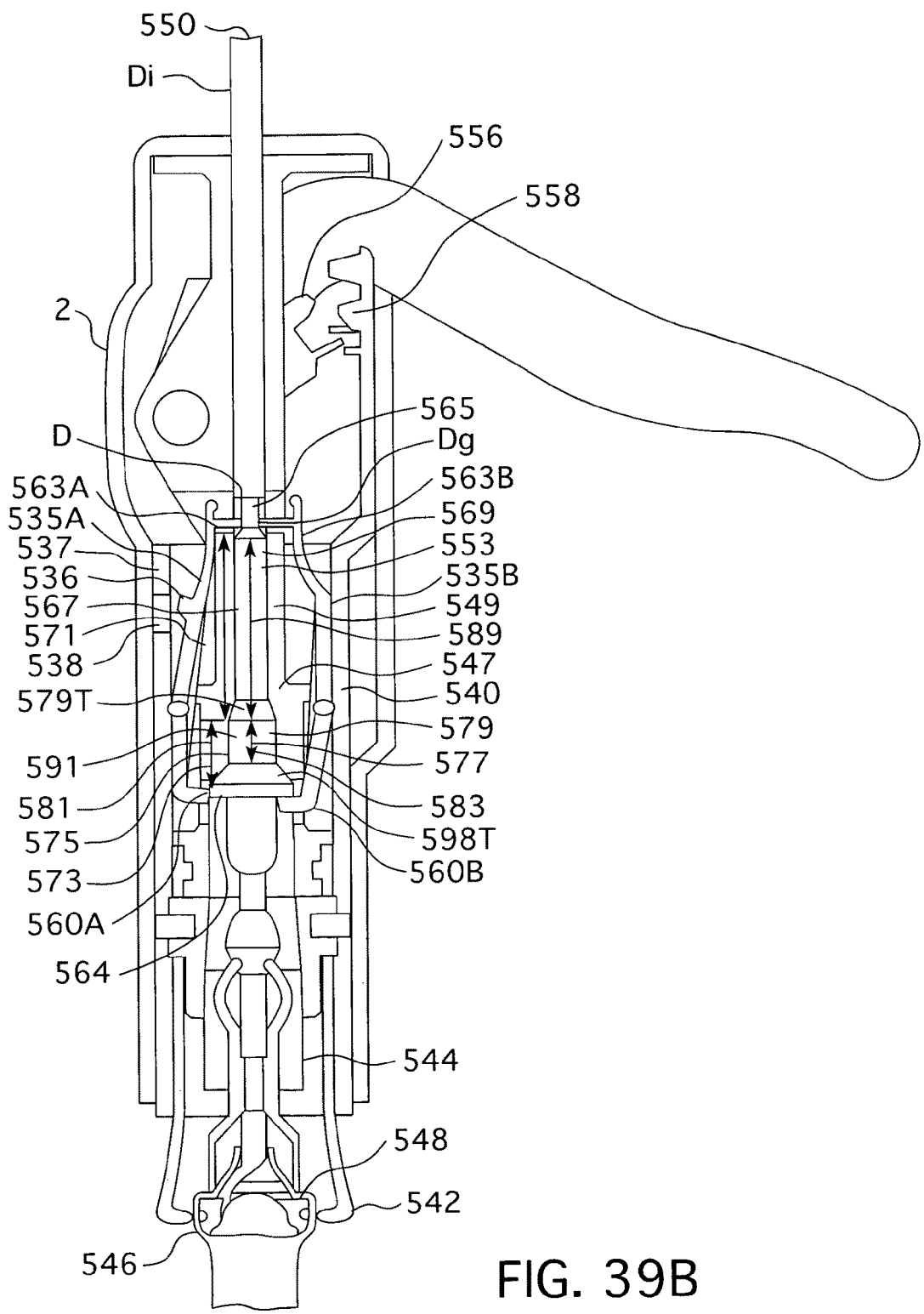

As shown in FIG. 39A, safety latch mechanism 535A can include safety latch 536 that can be retained in a hole or aperture 538 of clamp slide tube 540 to couple the clamp slide tube 540 with a core section 537 to prevent clamp slide tube 540 from moving up and down, thereby forming an integral radial clamping device and an axial cutting device. As ring component 550 is inserted into housing 2, large diameter mid-section 552 of ring component 550 causes safety latch 536 to pivot about pivot point 554 releasing clamp slide tube 540 (FIG. 39B). If the ring component 550 is not inserted properly, then safety latch mechanism 535A will not allow the clamp slide tube 540 to advance within housing 2. One embodiment of a large diameter mid-section 552 can be defined by a tapered section 551 ranging in diameter from an initial diameter Di of shaft 553 of ring component 550 to a maximum Dx along tapered section 551, which can be diameter De of tapered section end 564 (as shown in FIGS. 39A-E) or any other acceptable diametrical location depending on the configuration of tapered section 551. Safety latch mechanism 535B, having pivot point 554B, can include inward oriented tab 560 that travels along the outer surface 562 of ring component 550. As inward oriented tab 560 travels along surface 561 of tapered section 551 of large diameter mid-section 552, safety latch mechanism 535B elastically bends or deflects outward, pivots and springs back to make a clicking sound as inward oriented tab 560 passes tapered section end 564 of tapered section 551 of large diameter mid-section 552. The audible sound can be made by inward oriented tab 560 contacting shaft diameter Dc (where Dc is less than De as shown in FIG. 39B) or by a contact point 557 along inner surface 559 of safety latch mechanism 535B contacting a contact point along surface 561 (for example De) or both. Further, ring component 550 is now retained by housing 2 once inward oriented tab 560 passes tapered section end 564 of tapered section 551 of large diameter mid-section 552.

As an illustration of a mis-matched ring component and clamp, one embodiment includes a ring component with a tapered section 551 having a first diameter Di and a second diameter Dx smaller than the initial gap 527 between inward oriented tabs 560A, 560B prior to actuation of the device. The tapered section 551 passes through gap 527 without contacting an end 560A. Therefore, safety latch mechanism 535A does not pivot to release the safety latch 536A from hole or aperture 538 on an inner surface 593 of the actuation mechanism 521 and decouple actuation mechanism 521 from core section 537 to activate the clamping-cutting operation. The operable tapered section 551 must have a first diameter Di smaller than the initial gap 527 and a second diameter Dx greater than the initial gap 527 such that safety latch mechanism 535A pivots to release the safety latch 536A from hole or aperture 538.

Another locking mechanism is shown engaged in FIG. 39B. Safety latch mechanism 535A, 535B can either or both include inwardly oriented extensions 563A, 563B that pivotally rotate or spring into groove 565 of ring component 550 as ring component 550 advances into housing 2 to retain ring component 550 from further insertion into housing 2 or retraction from housing 2. As shown, safety latch mechanism 535A is slight shorter than safety latch mechanism 535B such that inward oriented tab 560A rests on tapered section end 564 to induce sufficient torque on to safety latch mechanism 535A causing safety latch mechanism 535A to pivot and position inwardly oriented extension 563A into groove 565. Inwardly oriented extension 563A can assert a sustained force onto to groove 565 or be free to pivot about pivot point 554 but only to the extent not to exceed the depth D of groove 565. Depth D is defined as half the difference of the shaft diameter Di to groove diameter Dg (Depth groove=(Di−Dg)/2). One embodiment of safety latch mechanism 535B is under constant bending load asserting a sustained force onto groove 565 to assure that inward oriented tab 560A springs back to contact ring component 550 to produce an audible sound.

Alternative configurations of safety latch mechanism 535A, 535B are contemplated that either safety latch mechanism can be under a constant load, intermittent load, or no load condition and still perform the desired functions of the present invention. For example, one embodiment (not shown) can include only safety latch mechanism 535A that retains ring component 550 and makes an audible sound when inwardly oriented extension 563A contacts groove 565. Another embodiment can include safety latch mechanism 535A without inwardly oriented tab 563A (not shown) and safety latch mechanism 535B with inwardly oriented extension 563B and inward oriented tab 560A as shown in FIGS. 39A-F. Yet another embodiment (not shown) can include safety latch mechanism 535A without inwardly oriented tab 563A and safety latch mechanism 535B with inwardly oriented extension 563B and inward oriented tab 560B both sized and spaced such that inwardly oriented extension 563B produces the audible sound when it contacts groove 565.

Figure 39C:
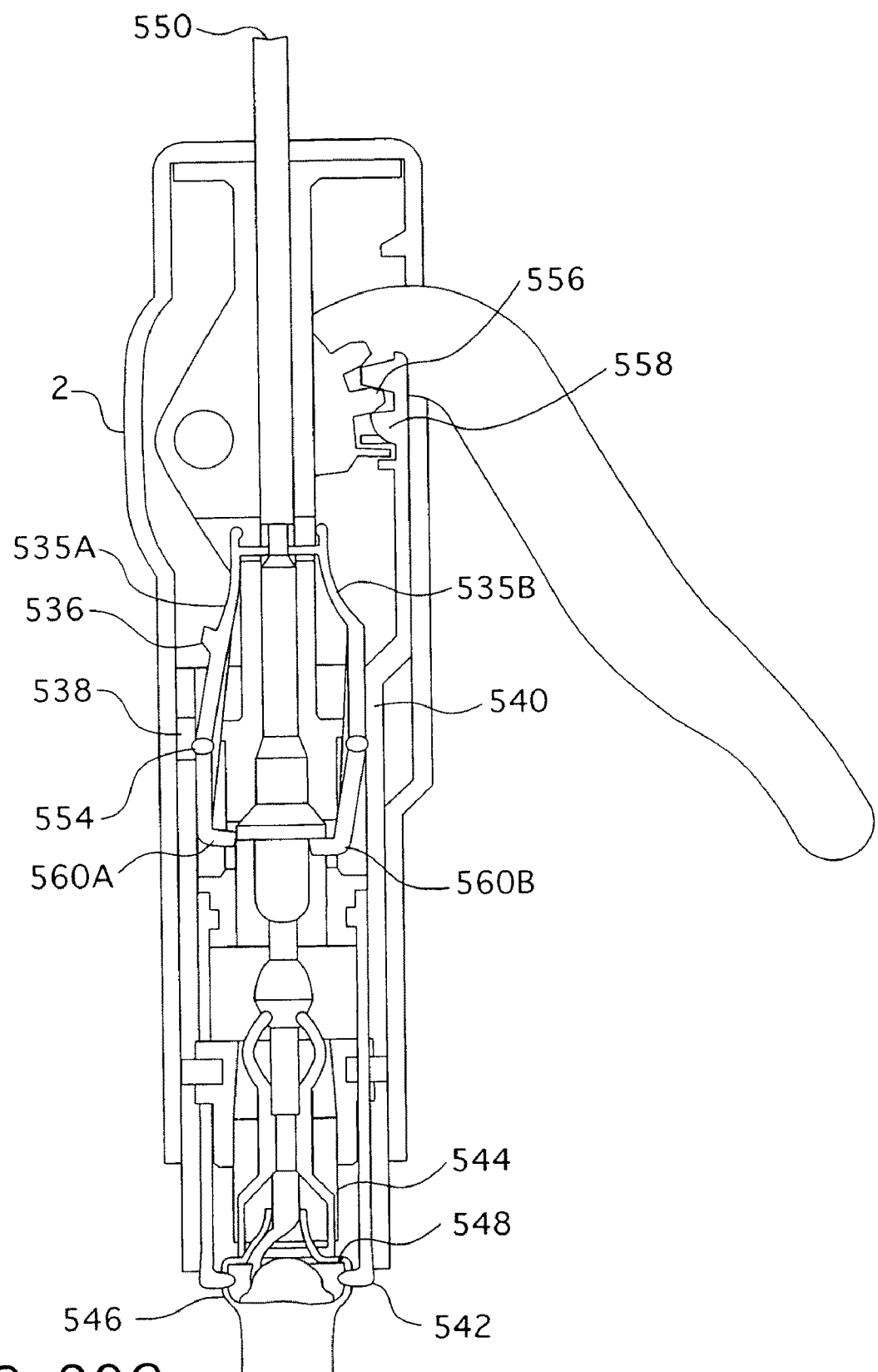
Figures 39D, 39E:
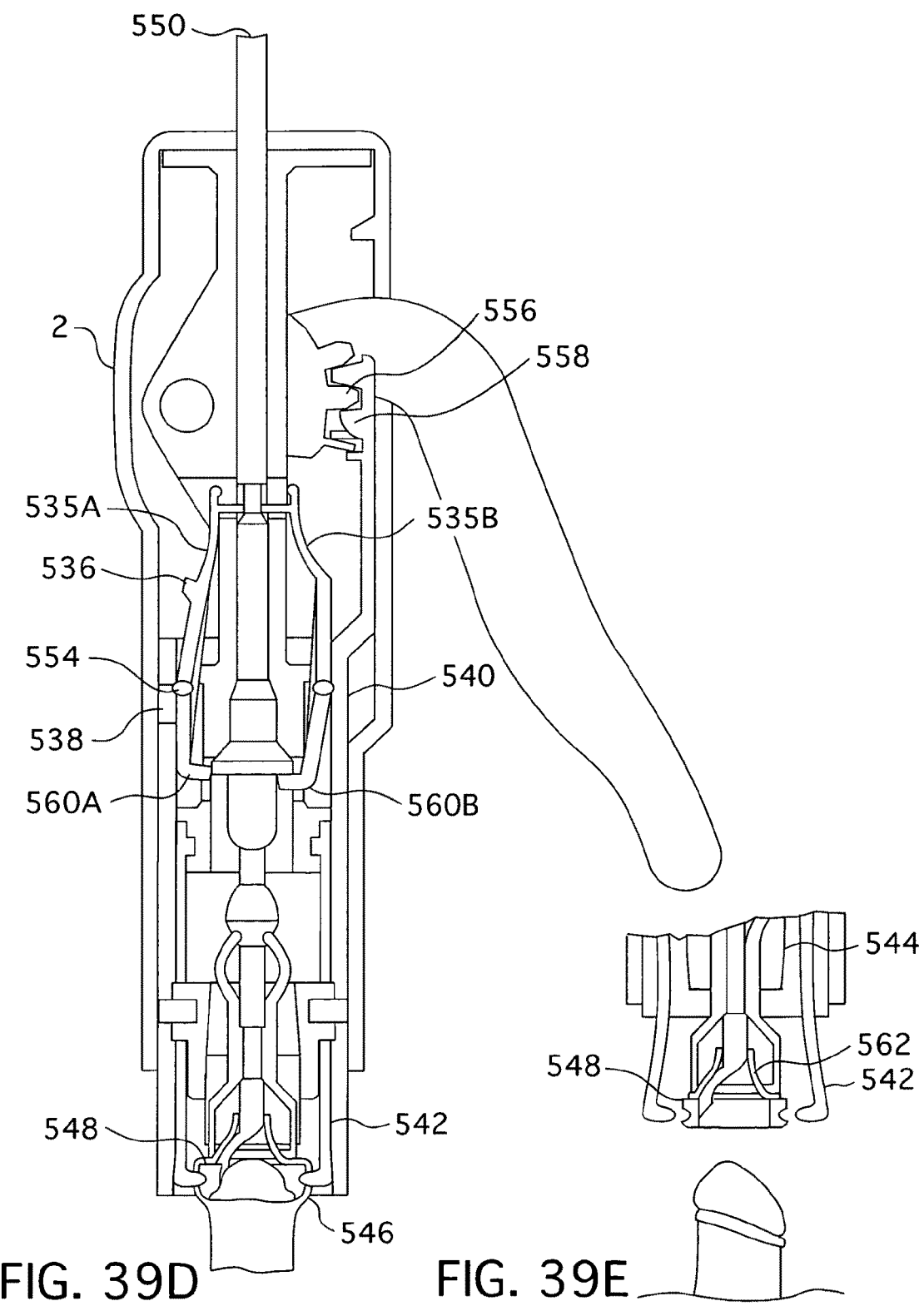

As shown in FIG. 39B-D, when clamp slide tube 540 advances downward, finger arms 542 close to clamp foreskin 546 and blade 544 is delivered to top surface 548 of ring component 550. Engagement gear 556 interacts with gear rack 558 to advance clamp slide tube 540 towards top surface 548 when ring component 550 is installed properly. Only a small force is required to initiate the two gears and move clamp slide tube 540 downward by actuation of lever arm 560. Once the next set of gears are engaged, the device can exert the large force required to crush and cut the foreskin 546.

However, when ring component 550 is installed improperly or not installed at all, slip gear tooth 556A will contact slip gear tooth 587 of the actuation mechanism 521 and elastically deflect or bend at a predetermined force and slip passed slip gear tooth 587, thereby disabling the lever arm 560 to protect the entire device from damage since clamp slide tube 540 is restrained from moving because safety latch 536 is retained in hole or aperture 538 of clamp slide tube 540. If slip gear 556A slips, nothing is broken and the device can still be used. Once the user recognizes slip gear 556A has slipped, the user can then lift lever arm 560 back to disengaged position and put in a correct ring component 550 to successfully use the device.

FIG. 39E illustrates a successful application of the present invention where the prepuce 562 stays with the device and is discarded after a single use.

Figure 39F:
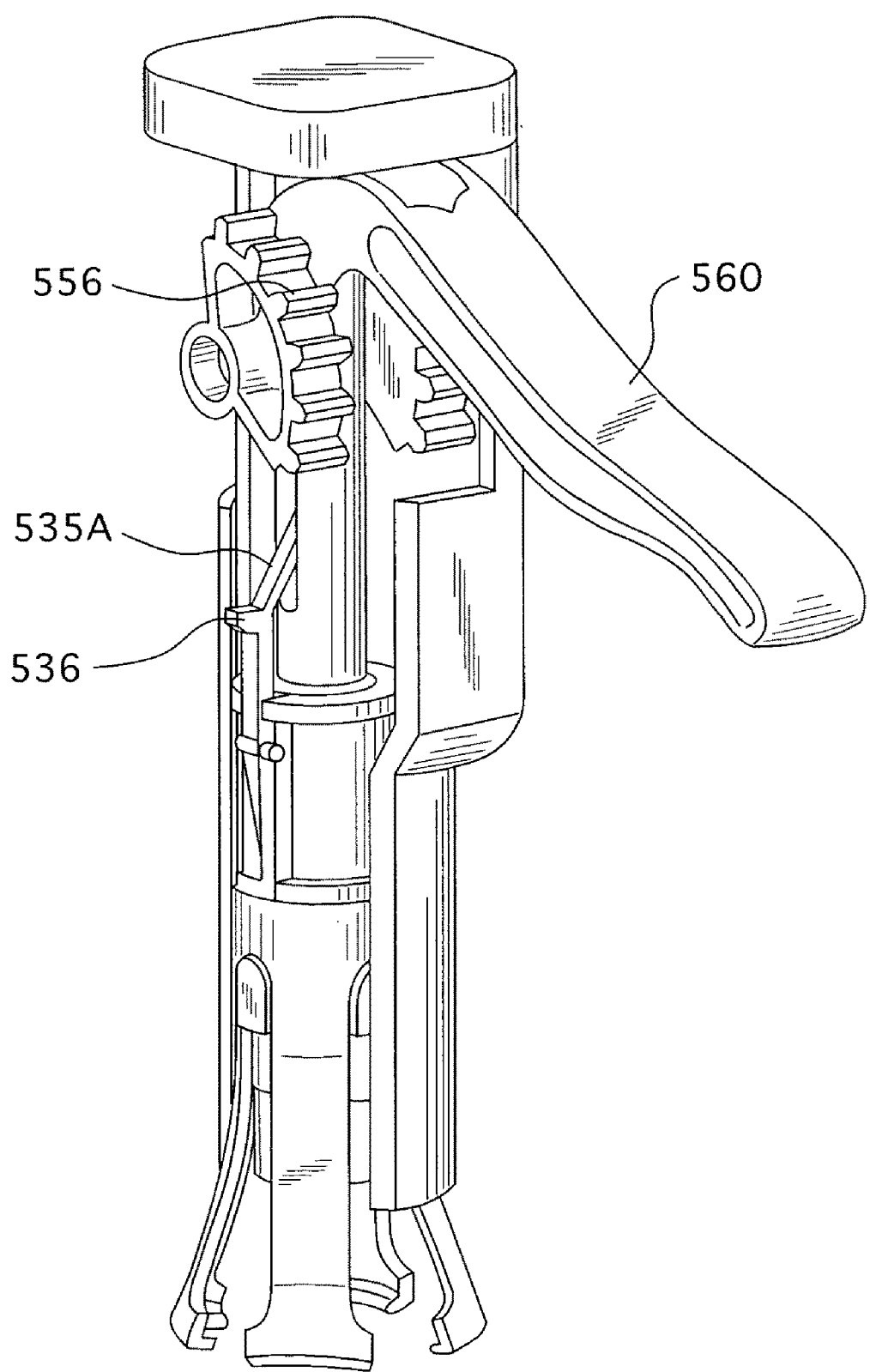
FIGS. 39F-G are pictorial views of one embodiment of the present invention having a slip gear and safety mechanism of FIGS. 39A-E illustrating the lever arm actuation and rotational travel when the ring shaft is properly inserted into the present invention.
Figure 39G:
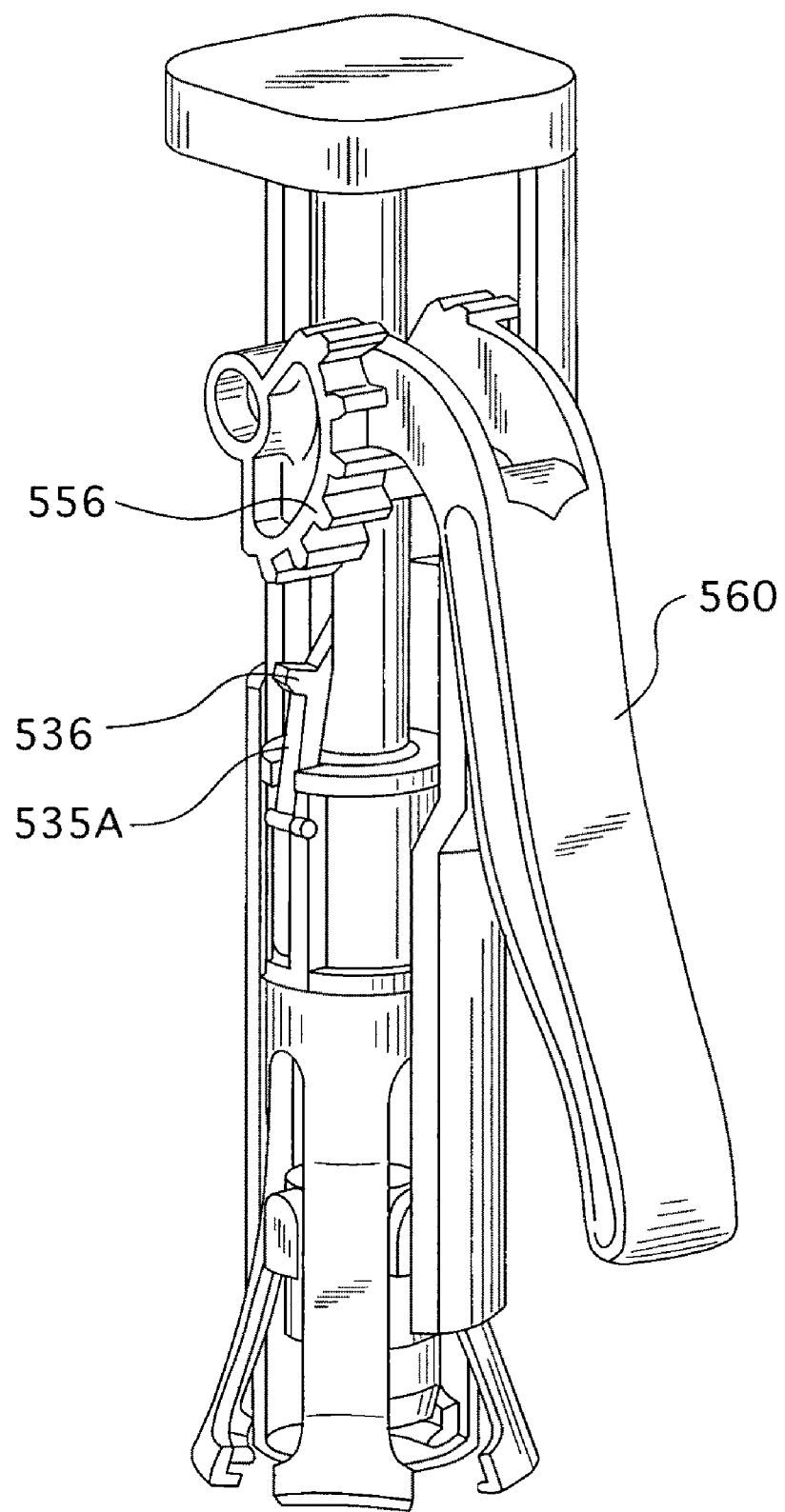

FIGS. 39F-G illustrate the adjacent orientation of lever arm 560 with respect to slip gear 556. It can be seen that when slip gear 556 slips, lever arm 560 will move independent of gear rack 558 since slip gear 556 and gear rack 558 are co-planar, whereas lever arm 560 is not in the same plane as slip gear 556 and gear rack 558.

Figure 40:
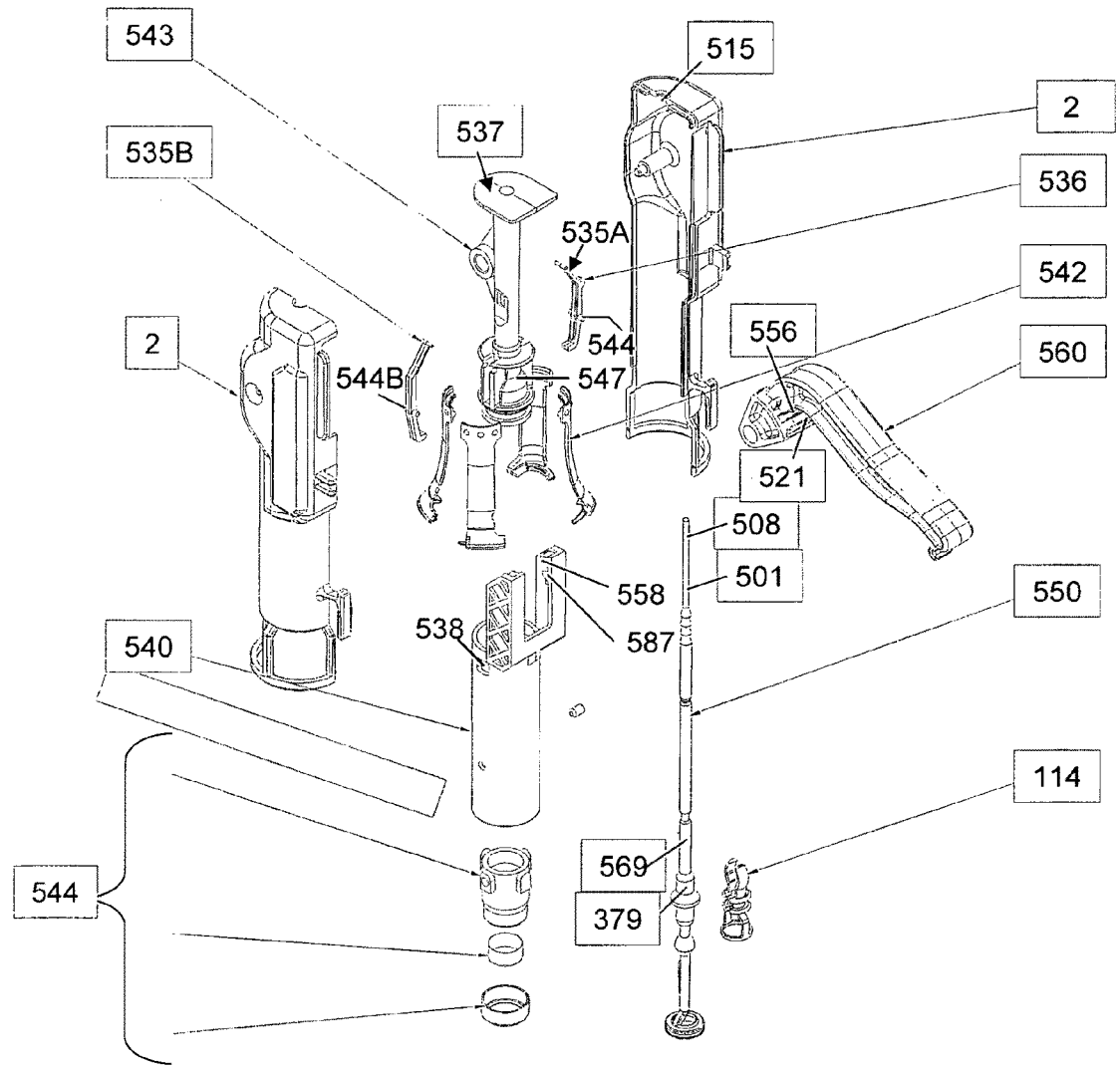
FIG. 40 is an exploded view of the present invention illustrated in FIGS. 39A-G.

FIG. 40 is an exploded view of the present invention illustrated in FIGS. 39A-G.

Further embodiments of the above disclosed components are disclosed in U.S. patent application Ser. No. 11/571,120 filed on Dec. 21, 2006, "Atraumatic Circumcision Device and Method to Use", by David R. Tomlinson, which is a U.S. national phase entry of Patent Cooperation Treaty international application serial number PCT/US2005/022404 filed on Jun. 23, 2005, "Atraumatic Circumcision Device and Method to Use", by David R. Tomlinson, which claims priority to U.S. provisional application Ser. No. 60/583,259 filed on Jun. 25, 2004, "Atraumatic Circumcision Ring and Method", by David R. Tomlinson, and U.S. patent application Ser. No. 11/768,808 filed on Jun. 26, 2007, "Self-Adjusting Pressure Applicator", by David R. Tomlinson, which claims priority to U.S. provisional application Ser. No. 60/816,798 filed on Jun. 26, 2006, whereby all above listed applications are herein incorporated by reference.

It will now be apparent to those skilled in the art that other embodiments, improvements, details, and uses can be made consistent with the letter and spirit of the foregoing disclosure and within the scope of this patent, which is limited only by the following claims, construed in accordance with the patent law, including the doctrine of equivalents.

While the disclosure has been described in detail and with reference to specific embodiments thereof, it will be apparent to one skilled in the art that various changes and modifications can be made therein without departing from the spirit and scope of the embodiments. Thus, it is intended that the present disclosure covers the modifications and variations of this disclosure provided they come within the scope of the appended claims and their equivalents.

What is claimed is:

1. A circumcision system for removing excess foreskin from a neonatal penis comprising:
 a ring component having a shaft with a ring at a proximal end, a tip at a distal end, and a tapered section between the proximal end and the distal end, wherein the tapered section includes a tapered section end, wherein the ring comprises a radially oriented clamping surface with a circumferential groove and an axially-oriented cutting surface; and
 a clamping-cutting device comprising: a two-piece housing forming a bore having a open end at a proximal end and a closed end having a hole at a distal end when assembled thereto, wherein the hole includes a diameter larger than a diameter of the tip of the shaft; a core section encased within the bore of the two-piece housing having an axially oriented blade disposed at a proximal end and a lever arm pivot point at a distal end; a lever arm having an engagement tooth being pivotally attached to the lever arm pivot point of the core section; a pair of safety latch mechanisms pivotally attached to the core section, wherein the pair of safety latch mechanisms form a pre-actuation gap therebetween; wherein each safety latch mechanism of the pair of safety latch mechanisms includes two ends and an inward oriented tab connected to at least one end of the two ends to engage the tapered section end of the ring component tapered section to retain the ring component in place relative to the two-piece housing; and an actuation mechanism disposed within the bore of the two-piece housing comprising a plurality of longitudinal clamping arms at a proximal end of the actuation mechanism having inward radial projections, wherein at least a portion of the plurality of longitudinal clamping arms being disposed outside the bore of the housing forming a gap between the inward radial projections being greater than a diameter of the circumferential groove of the radially oriented clamping surface of the ring component; and a lever arm engagement gear tooth at a distal end of the actuation mechanism to engage the engagement tooth of the lever arm when the lever arm is actuated with the proper ring component inserted therein.

2. The circumcision system according to claim 1, wherein: the ring component further comprises a limiting section having a first section with a first diameter and a first section length, a second section with a second diameter greater than the first diameter, and a second section length; and wherein the core section further comprises a limiting section having a first section with a bore diameter greater than the first diameter of the first limiting section of the shaft to receive the shaft of the ring component there-through and a first section depth, and a second section with a bore diameter greater than the second diameter of the second limiting section of the shaft and a second section depth, wherein the second section depth of the second limiting section of the core section is substantially equal to the second section length of the second limiting section of the ring component.

3. The circumcision system according to claim 1, wherein at least one of the safety mechanisms of the pair of safety latch mechanisms comprises a safety latch to engage an aperture on an inner surface of the actuation mechanism; wherein the tapered section of the ring component further comprises a first diameter smaller than the pre-actuation gap formed by the pair of safety latch mechanisms and a second diameter greater than the pre-actuation gap formed by the pair of safety latch mechanisms such that at least one safety latch mechanism of the pair of safety latch mechanisms pivots to release the safety latch from the aperture on the inner surface of the actuation mechanism when the second diameter of the tapered section of the ring component contacts an end of the at least one safety latch mechanism of the pair of safety latch mechanisms.

4. The circumcision system according to claim 1, wherein at least one safety latch mechanism of the pair of safety latch mechanisms comprises a safety latch; and wherein the actuation mechanism further comprises an aperture on an inner surface of the actuation mechanism sized to retain the safety latch of the at least one safety latch mechanism thereby retaining relative movement of the actuation mechanism with respect to the core section.

5. The circumcision system according to claim 1, wherein the lever arm further comprises a slip gear tooth and wherein the actuation mechanism further comprises a slip gear tooth to engage the slip gear tooth of the lever arm when the lever arm is actuated for a clamping-cutting operation.

6. The circumcision system according to claim 1, wherein the two-piece housing further comprises an extension attached to the proximal end having an outer surface that contacts body tissue as the neonatal penis is guided through a bore of the extension toward the housing to ensure the penis is extended a predetermined distance.

7. The circumcision system according to claim 1, wherein each inward radial projection of the plurality of longitudinal clamping arms comprise a tongue and a groove such that the tongue of an inward radial projection is received within the groove of an adjacent inward radial projection to form a circumferentially overlapping configuration therewith and no radial-through gap therebetween when the plurality of longitudinal clamping arms are in a pre-clamp position to prevent foreskin migrating between the inward radial projections during a clamping operation and pinching the foreskin.

* * * * *